(12) United States Patent
Worrell et al.

(10) Patent No.: US 11,406,443 B2
(45) Date of Patent: *Aug. 9, 2022

(54) ARTICULATION JOINT FEATURES FOR ARTICULATING SURGICAL DEVICE

(71) Applicant: Cilag GmbH International, Zug (CH)

(72) Inventors: Barry C. Worrell, Centerville, OH (US); David K. Norvell, Monroe, OH (US); Charles J. Scheib, Loveland, OH (US); Frederick E. Shelton, IV, Hillsboro, OH (US); Geoffrey S. Strobl, Williamsburg, OH (US); Jeffrey S. Swayze, West Chester, OH (US); Gregory A. Trees, Loveland, OH (US); Jason E. Zerkle, Blanchester, OH (US); Kevin M. Montgomery, Morrow, OH (US)

(73) Assignee: Cilag GmbH International, Zug (CH)

( * ) Notice: Subject to any disclaimer, the term of this patent is extended or adjusted under 35 U.S.C. 154(b) by 49 days.

This patent is subject to a terminal disclaimer.

(21) Appl. No.: 16/875,602

(22) Filed: May 15, 2020

(65) Prior Publication Data

US 2020/0383722 A1 Dec. 10, 2020

Related U.S. Application Data

(60) Division of application No. 15/651,112, filed on Jul. 17, 2017, now Pat. No. 10,660,696, which is a
(Continued)

(51) Int. Cl.
*A61B 18/14* (2006.01)
*A61B 18/00* (2006.01)
(Continued)

(52) U.S. Cl.
CPC ...... *A61B 18/1447* (2013.01); *A61B 18/1445* (2013.01); *A61B 2017/00314* (2013.01);
(Continued)

(58) Field of Classification Search
CPC ..... A61B 18/00; A61B 18/14; A61B 18/1492; A61B 2018/00053; A61B 2018/00184; A61B 2018/00202
See application file for complete search history.

(56) References Cited

U.S. PATENT DOCUMENTS 2,715,341 A 8/1955 Hogan
2,818,744 A 1/1958 Moody
(Continued)

FOREIGN PATENT DOCUMENTS

DE 4300307 7/1994
EP 1637086 3/2006
(Continued)

OTHER PUBLICATIONS

Australian Examiner's Report dated Jul. 25, 2013 for Application No. 2011305410.
(Continued)

*Primary Examiner* — Allen Porter
(74) *Attorney, Agent, or Firm* — Frost Brown Todd LLC

(57) ABSTRACT

An electrosurgical device comprises a body, an end effector, a cutting member, and a shaft. The end effector includes a pair of jaws that are operable to deliver RF energy to tissue that is clamped between the jaws. The cutting member is operable to sever tissue that is clamped between the jaws. The shaft extends between the body and the end effector. The shaft includes an articulation section that is operable to selectively position the end effector at non-parallel positions relative to the longitudinal axis of the shaft. Some versions include a rotation section that is distal to the articulation
(Continued)

section. The rotation section is operable to rotate the end effector relative to the articulation section.

20 Claims, 16 Drawing Sheets

Related U.S. Application Data continuation of application No. 15/204,083, filed on Jul. 7, 2016, now Pat. No. 9,730,753, which is a continuation of application No. 13/235,660, filed on Sep. 19, 2011, now Pat. No. 9,402,682.

(60) Provisional application No. 61/386,117, filed on Sep. 24, 2010.

(51) Int. Cl.
  *A61B 17/00* (2006.01)
  *A61B 18/12* (2006.01)

(52) U.S. Cl.
  CPC ............. *A61B 2018/0063* (2013.01); *A61B 2018/00601* (2013.01); *A61B 2018/126* (2013.01); *A61B 2018/1455* (2013.01)

(56) References Cited

U.S. PATENT DOCUMENTS

| | | |
|---|---|---|
| 2,857,776 A | 10/1958 | Williams |
| 2,881,645 A | 4/1959 | Kruchten |
| 3,194,530 A | 7/1965 | Heyl |
| 4,203,430 A | 5/1980 | Takahashi |
| 4,483,562 A | 11/1984 | Schoolman |
| 4,723,936 A | 2/1988 | Buchbinder et al. |
| 4,880,015 A | 11/1989 | Nierman |
| 4,945,920 A | 8/1990 | Clossick |
| 5,003,989 A | 4/1991 | Taylor et al. |
| 5,020,514 A | 6/1991 | Heckele |
| 5,125,895 A | 6/1992 | Buchbinder et al. |
| 5,330,502 A | 7/1994 | Hassler et al. |
| 5,383,888 A | 1/1995 | Zvenyatsky et al. |
| 5,391,180 A | 2/1995 | Tovey et al. |
| 5,395,329 A | 3/1995 | Fleischhacker et al. |
| 5,411,519 A | 5/1995 | Tovey et al. |
| 5,441,499 A | 8/1995 | Fritzsch |
| 5,454,827 A | 10/1995 | Aust et al. |
| 5,462,546 A | 10/1995 | Rydell |
| 5,514,130 A | 5/1996 | Baker |
| 5,514,157 A | 5/1996 | Nicholas et al. |
| 5,540,685 A | 7/1996 | Parins et al. |
| 5,549,637 A | 8/1996 | Crainich |
| 5,562,682 A | 10/1996 | Oberlin et al. |
| 5,607,450 A | 3/1997 | Zvenyatsky et al. |
| 5,609,601 A | 3/1997 | Kolesa et al. |
| 5,632,432 A | 5/1997 | Schulze et al. |
| 5,643,294 A | 7/1997 | Tovey et al. |
| 5,673,840 A | 10/1997 | Schulze et al. |
| 5,700,275 A | 12/1997 | Bell et al. |
| 5,743,456 A | 4/1998 | Jones et al. |
| 5,766,196 A | 6/1998 | Griffiths |
| 5,766,205 A | 6/1998 | Zvenyatsky et al. |
| 5,782,859 A | 7/1998 | Nicholas et al. |
| 5,921,956 A | 7/1999 | Grinberg et al. |
| 5,931,832 A | 8/1999 | Jensen |
| 6,162,208 A | 12/2000 | Hipps |
| 6,179,809 B1 | 1/2001 | Khairkhahan et al. |
| 6,423,059 B1 | 7/2002 | Hanson et al. |
| 6,500,176 B1 | 12/2002 | Truckai et al. |
| 6,554,794 B1 | 4/2003 | Mueller et al. |
| RE38,335 E | 11/2003 | Aust et al. |
| 6,656,177 B2 | 12/2003 | Truckai et al. |
| 6,682,493 B2 | 1/2004 | Mirigian et al. |
| 6,783,524 B2 | 8/2004 | Anderson et al. |
| 6,817,974 B2 | 11/2004 | Cooper et al. |
| 6,905,497 B2 | 6/2005 | Truckai et al. |
| 6,991,627 B2 | 1/2006 | Madhani et al. |
| 7,004,938 B2 | 2/2006 | Ormsby et al. |
| 7,070,595 B2 | 7/2006 | Ormsby et al. |
| 7,081,114 B2 | 7/2006 | Rashidi |
| 7,083,620 B2 | 8/2006 | Jahns et al. |
| 7,087,071 B2 | 8/2006 | Nicholas et al. |
| 7,112,201 B2 | 9/2006 | Truckai et al. |
| 7,125,409 B2 | 10/2006 | Truckai et al. |
| 7,141,897 B2 | 11/2006 | Park |
| 7,150,749 B2 | 12/2006 | Dycus et al. |
| 7,156,846 B2 | 1/2007 | Dycus et al. |
| 7,159,750 B2 | 1/2007 | Racenet et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,208,005 B2 | 4/2007 | Frecker et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,338,513 B2 | 3/2008 | Lee et al. |
| 7,354,440 B2 | 4/2008 | Truckal et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,407,076 B2 | 8/2008 | Racenet et al. |
| 7,410,483 B2 | 8/2008 | Danitz et al. |
| 7,424,965 B2 | 9/2008 | Racenet et al. |
| 7,434,716 B2 | 10/2008 | Viola |
| 7,455,208 B2 | 11/2008 | Wales et al. |
| 7,464,849 B2 | 12/2008 | Shelton, IV et al. |
| 7,481,348 B2 | 1/2009 | Marczyk |
| 7,494,039 B2 | 2/2009 | Racenet et al. |
| 7,506,790 B2 | 3/2009 | Shelton, IV |
| 7,540,872 B2 | 6/2009 | Schechter et al. |
| 7,549,564 B2 | 6/2009 | Boudreaux |
| 7,553,275 B2 | 6/2009 | Padget et al. |
| 7,559,450 B2 | 7/2009 | Wales et al. |
| 7,584,880 B2 | 9/2009 | Racenet et al. |
| 7,588,175 B2 | 9/2009 | Timm et al. |
| 7,594,913 B2 | 9/2009 | Ormsby et al. |
| 7,597,230 B2 | 10/2009 | Racenet et al. |
| 7,608,083 B2 | 10/2009 | Lee et al. |
| 7,615,044 B2 | 11/2009 | Scheibe et al. |
| 7,651,494 B2 | 1/2010 | McClurken et al. |
| 7,654,431 B2 | 2/2010 | Hueil et al. |
| 7,691,095 B2 | 4/2010 | Bednarek et al. |
| 7,703,653 B2 | 4/2010 | Shah et al. |
| 7,708,182 B2 | 5/2010 | Viola |
| 7,721,935 B2 | 5/2010 | Racenet et al. |
| 7,771,425 B2 | 8/2010 | Dycus et al. |
| 7,780,054 B2 | 8/2010 | Wales |
| 7,784,662 B2 | 8/2010 | Wales et al. |
| 7,784,663 B2 | 8/2010 | Shelton, IV |
| 7,793,814 B2 | 9/2010 | Racenet et al. |
| 7,798,386 B2 | 9/2010 | Schall et al. |
| 7,799,028 B2 | 9/2010 | Schechter et al. |
| 7,815,090 B2 | 10/2010 | Marczyk |
| 7,815,091 B2 | 10/2010 | Marczyk |
| 7,815,637 B2 | 10/2010 | Ormsby et al. |
| 7,828,725 B2 | 11/2010 | Maruyama |
| 7,909,220 B2 | 3/2011 | Viola |
| 8,006,365 B2 | 8/2011 | Levin et al. |
| 8,033,441 B2 | 10/2011 | Marczyk |
| 8,062,306 B2 | 11/2011 | Nobis et al. |
| 8,092,451 B2 | 1/2012 | Schechter et al. |
| 8,100,309 B2 | 1/2012 | Marczyk |
| 8,142,473 B2 | 3/2012 | Cunningham |
| 8,152,799 B2 | 4/2012 | Ormsby et al. |
| 8,161,838 B2 | 4/2012 | Duval |
| 8,197,479 B2 | 6/2012 | Olson et al. |
| 8,205,619 B2 | 6/2012 | Shah et al. |
| 8,236,010 B2 | 8/2012 | Ortiz et al. |
| 8,241,320 B2 | 8/2012 | Lyons et al. |
| 8,245,594 B2 | 8/2012 | Rogers et al. |
| 8,292,147 B2 | 10/2012 | Viola |
| 8,292,889 B2 | 10/2012 | Cunningham et al. |
| 8,317,811 B2 | 11/2012 | Laporte Rosello et al. |
| 8,323,239 B2 | 12/2012 | Bednarek et al. |

(56) References Cited

U.S. PATENT DOCUMENTS

| | | |
|---|---|---|
| 8,323,297 B2 | 12/2012 | Hinman et al. |
| 8,353,902 B2 | 1/2013 | Prakash |
| 8,357,161 B2 | 1/2013 | Mueller |
| 8,361,067 B2 | 1/2013 | Pellegrino et al. |
| 8,366,709 B2 | 2/2013 | Schechter et al. |
| 8,372,064 B2 | 2/2013 | Douglass et al. |
| 8,377,059 B2 | 2/2013 | Deville et al. |
| 8,403,832 B2 | 3/2013 | Cunningham et al. |
| 8,419,747 B2 | 4/2013 | Hinman et al. |
| 8,439,912 B2 | 5/2013 | Cunningham et al. |
| 8,444,637 B2 | 5/2013 | Podmore et al. |
| 8,475,453 B2 | 7/2013 | Marczyk et al. |
| 8,540,711 B2 | 9/2013 | Dycus et al. |
| 8,551,084 B2 | 10/2013 | Hauck et al. |
| 8,556,850 B2 | 10/2013 | Tegg |
| 8,617,087 B2 | 12/2013 | Schultz |
| 8,622,274 B2 | 1/2014 | Yates et al. |
| 8,628,545 B2 | 1/2014 | Cabrera et al. |
| 8,631,988 B2 | 1/2014 | Viola |
| 8,632,539 B2 | 1/2014 | Twomey et al. |
| 8,647,341 B2 | 2/2014 | Dycus et al. |
| 8,676,290 B2 | 3/2014 | Tegg |
| 8,767,970 B2 | 7/2014 | Eppolito |
| 8,770,459 B2 | 7/2014 | Racenet et al. |
| 8,858,495 B2 | 10/2014 | Tegg et al. |
| 8,870,867 B2 | 10/2014 | Walberg et al. |
| 8,906,019 B2 | 12/2014 | Mueller |
| 8,929,589 B2 | 1/2015 | Publicover et al. |
| 8,931,683 B2 | 1/2015 | Racenet et al. |
| 8,939,974 B2 | 1/2015 | Boudreaux et al. |
| 8,968,355 B2 | 3/2015 | Malkowski et al. |
| 9,055,961 B2 | 6/2015 | Manzo et al. |
| 9,089,327 B2 | 7/2015 | Worrell et al. |
| 9,113,902 B2 | 8/2015 | Cunningham et al. |
| 9,132,258 B2 | 9/2015 | Bednarek et al. |
| 9,149,274 B2 | 10/2015 | Spivey et al. |
| 9,149,324 B2 | 10/2015 | Huang et al. |
| 9,155,586 B2 | 10/2015 | Suzuki |
| 9,161,803 B2 | 10/2015 | Yates et al. |
| 9,220,559 B2 | 12/2015 | Worrell et al. |
| 9,339,287 B2 | 5/2016 | Hassoun |
| 9,351,751 B2 | 5/2016 | Malkowski |
| 9,402,682 B2 | 8/2016 | Worrell et al. |
| 9,440,364 B2 | 9/2016 | Danitz et al. |
| 9,545,253 B2 | 1/2017 | Worrell et al. |
| 9,730,753 B2 | 8/2017 | Worrell et al. |
| 9,877,720 B2 | 1/2018 | Worrell et al. |
| 9,968,397 B2 | 5/2018 | Taylor et al. |
| 10,660,696 B2 | 5/2020 | Worrell et al. |
| 2003/0114851 A1 | 6/2003 | Truckai et al. |
| 2006/0190034 A1 | 8/2006 | Nishizawa et al. |
| 2006/0259071 A1 | 11/2006 | Nicholas et al. |
| 2007/0219550 A1 | 9/2007 | Thompson et al. |
| 2007/0219581 A1 | 9/2007 | Dohi et al. |
| 2007/0250072 A1 | 10/2007 | Weitzner et al. |
| 2007/0282324 A1 | 12/2007 | Vaska et al. |
| 2007/0282358 A1 | 12/2007 | Remiszewski et al. |
| 2009/0171354 A1 | 7/2009 | Deville et al. |
| 2010/0298824 A1 | 11/2010 | Rothstein et al. |
| 2011/0009863 A1 | 1/2011 | Marczyk et al. |
| 2011/0028991 A1 | 2/2011 | Ikeda et al. |
| 2011/0213360 A1 | 9/2011 | Cunningham et al. |
| 2012/0078244 A1 | 3/2012 | Worrell et al. |
| 2012/0109186 A1 | 5/2012 | Parrott et al. |
| 2012/0253326 A1 | 10/2012 | Kleyman |
| 2012/0265186 A1 | 10/2012 | Burger et al. |
| 2013/0131651 A1 | 5/2013 | Strobl et al. |
| 2016/0270839 A1* | 9/2016 | Stewart ............. A61B 18/1445 |

FOREIGN PATENT DOCUMENTS

| | | |
|---|---|---|
| EP | 2151204 | 2/2010 |
| FR | 2915873 | 11/2008 |
| JP | H08-0336540 | 12/1996 |
| JP | 2005-511259 A | 4/2005 |
| JP | 2008-511404 A | 4/2008 |
| JP | 2008-521485 A | 6/2008 |
| JP | 2008-220972 A | 9/2008 |
| JP | 2010-036039 A | 2/2010 |
| JP | 2010-505522 A | 2/2010 |
| WO | WO 2000/67834 | 11/2000 |
| WO | WO 2008/045348 | 4/2008 |
| WO | WO 2008/045394 | 4/2008 |
| WO | WO 2010/104755 | 9/2010 |
| WO | WO 2012/067468 | 5/2012 |
| WO | WO 2012/078951 | 6/2012 |

OTHER PUBLICATIONS

Australian Examiner's Report dated Jul. 29, 2013 for Application No. 2011305403.
Australian Full Examiner's Report dated Apr. 15, 2015 for Application No. 2011305403.
Brazilian Office Action dated Dec. 5, 2019 for Application No. BR112013006517-6.
Canadian Office Action dated Jul. 11, 2017 for Application No. 2,811,298.
Canadian Office Action dated May 16, 2018 for Application No. 2,811,298.
Canadian Office Action dated Jul. 11, 2017 for Application No. 2,811,339.
Chinese First Office Action dated Jan. 6, 2015 for Application No. 201180046071.X.
Chinese Second Office Action dated Sep. 9, 2015 for Application No. 201180046071.X.
Chinese First Office Action dated Dec. 3, 2014 for Application No. 201180046162.3.
Chinese Second Office Action dated Aug. 28, 2015 for Application No. CN 201180046162.3.
Indian Office Action dated Jul. 15, 2019 for Application No. 2100/DELNP/2013.
Indian Office Action dated Jul. 23, 2019 for Application No. 2108/DELNP/2013.
International Search Report and Written Opinion dated Jan. 24, 2012 for International Application No. PCT/US2011/052734.
International Search Report and Written Opinion dated Feb. 1, 2012 for International Application No. PCT/US2011/052723.
International Search Report and Written Opinion dated Mar. 19, 2012 for International Application No. PCT/US2011/053028.
Japanese Notification of Reasons for Refusal dated Jun. 23, 2015 for Application No. 2013-530306.
Japanese Notification of Reasons for Refusal dated Jul. 21, 2015 for Application No. 2013-530307.
U.S. Appl. No. 61/386,117, filed Sep. 24, 2010.
U.S. Appl. No. 61/410,603, filed Nov. 5, 2010.

* cited by examiner

ARTICULATION JOINT FEATURES FOR ARTICULATING SURGICAL DEVICE

PRIORITY

This application is a divisional of U.S. patent application Ser. No. 15/651,112, entitled "Articulation Joint Features For Articulating Surgical Device," filed Jul. 17, 2017 and issued as U.S. Pat. No. 10,660,696 on May 26, 2020, which is a continuation of U.S. patent application Ser. No. 15/204,083, entitled "Articulation Joint Features For Articulating Surgical Device," filed Jul. 7, 2016 and issued as U.S. Pat. No. 9,730,753 on Aug. 15, 2017, which is a continuation of U.S. patent application Ser. No. 13/235,660, entitled "Articulation Joint Features For Articulating Surgical Device," filed Sep. 19, 2011 and issued as U.S. Pat. No. 9,402,682 on Aug. 2, 2016, which claims priority to U.S. Provisional Application Ser. No. 61/386,117, filed Sep. 24, 2010, entitled "Articulating Surgical Device," the disclosure of which is incorporated by reference herein.

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, now U.S. Pat. No. 9,161,803, issued Oct. 20, 2015, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

BACKGROUND

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
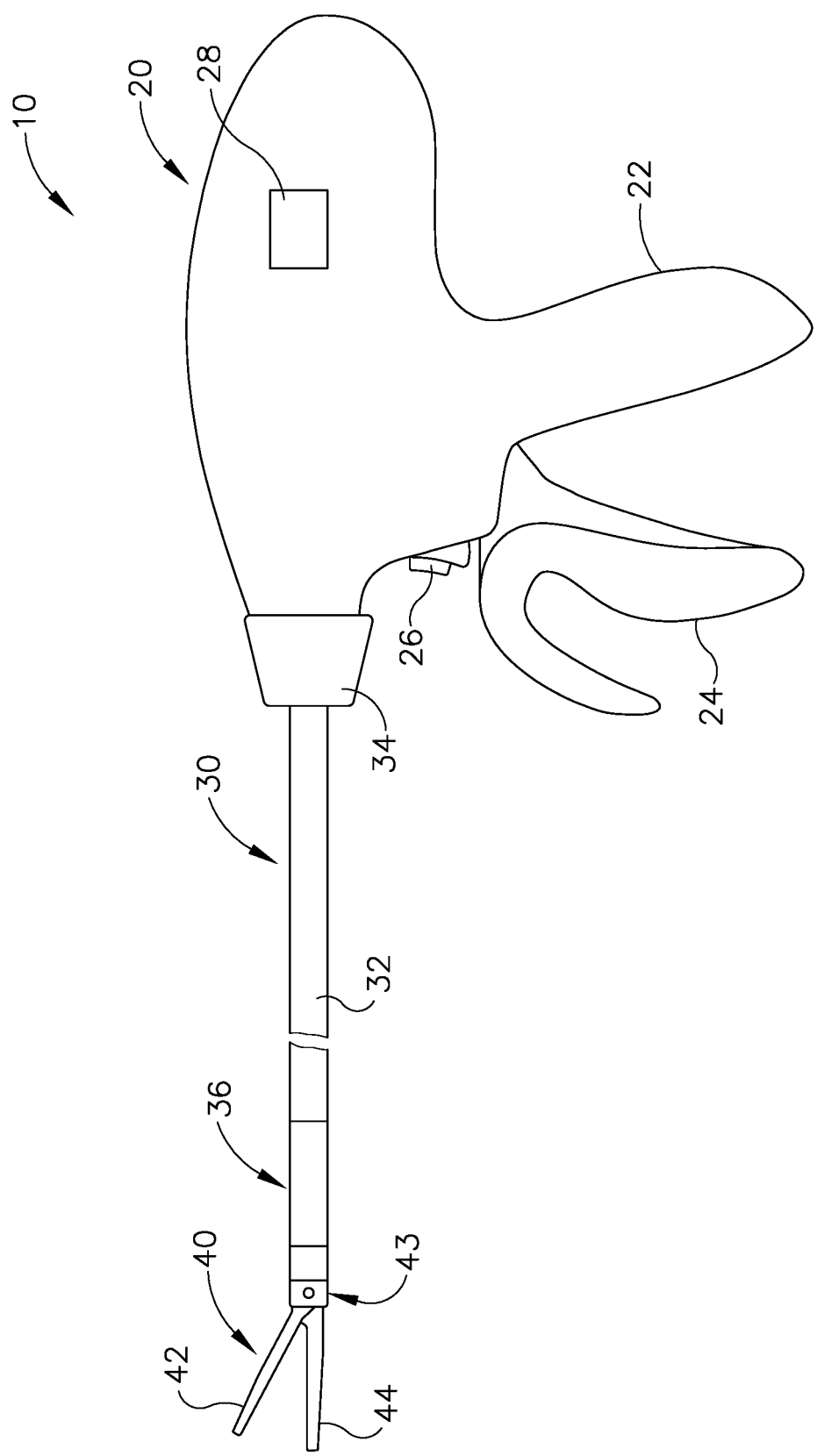
FIG. 1 depicts a side elevational view of an exemplary electrosurgical medical device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, now U.S. Pat. No. 8,939,974; and/or U.S. patent application Ser. No. 13/151,481, now U.S. Pat. No. 9,161,803. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. It should be understood that pistol grip (22), trigger (24), and button (26) may be modified, substituted, supplemented, etc. in any suitable way, and that the descriptions of such components herein are merely illustrative. Articulation control (28) of the present example is operable to selectively control articulation section (36) of shaft (30), which will be described in greater detail below. Various examples of forms that articulation control (28) may take will also be described in greater detail below, while further examples will be apparent to those of ordinary skill in the art in view of the teachings herein.

Shaft (30) of the present example includes an outer sheath (32) and an articulation section (36). Articulation section (36) is operable to selectively position end effector (40) at various angles relative to the longitudinal axis defined by sheath (32). Various examples of forms that articulation section (36) and other components of shaft (30) may take will be described in greater detail below, while further examples will be apparent to those of ordinary skill in the art in view of the teachings herein. For instance, it should be understood that various components that are operable to actuate articulation section (36) may extend through the interior of sheath (32). In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
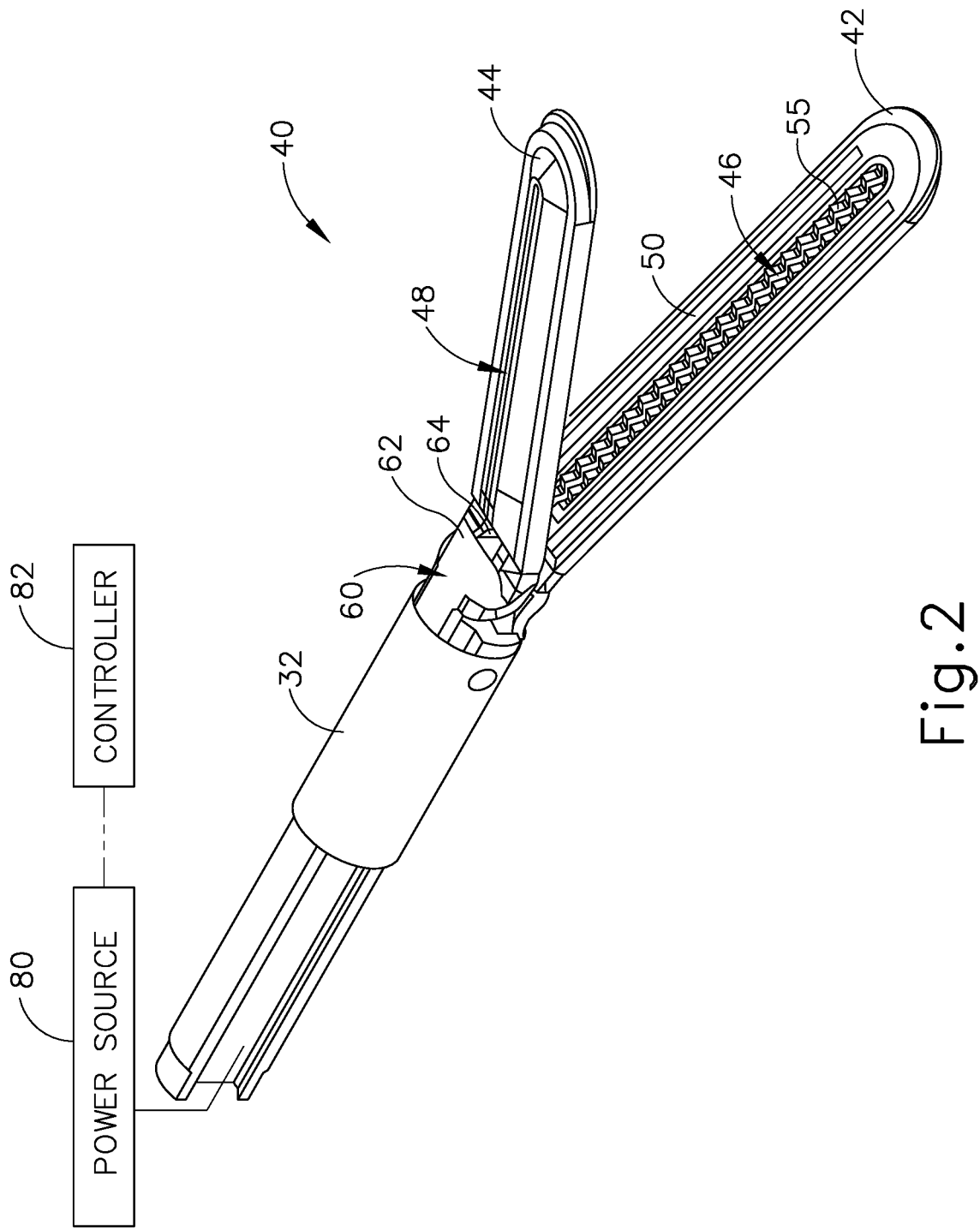
FIG. 2 depicts a perspective view of the end effector of the device of FIG. 1, in an open configuration.
Figure 3:
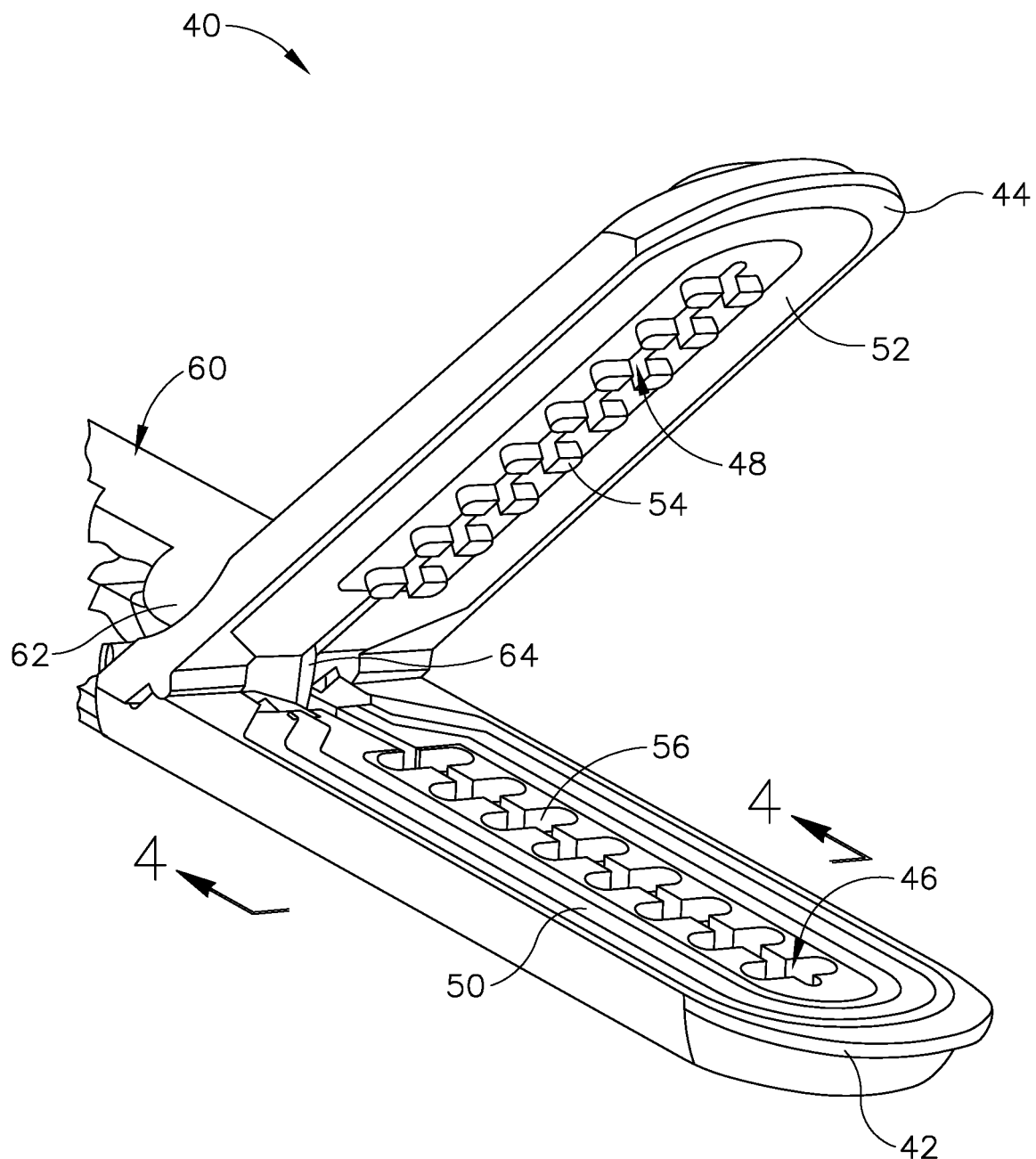
FIG. 3 depicts another perspective view of the end effector of the device of FIG. 1, in an open configuration.
Figure 4:
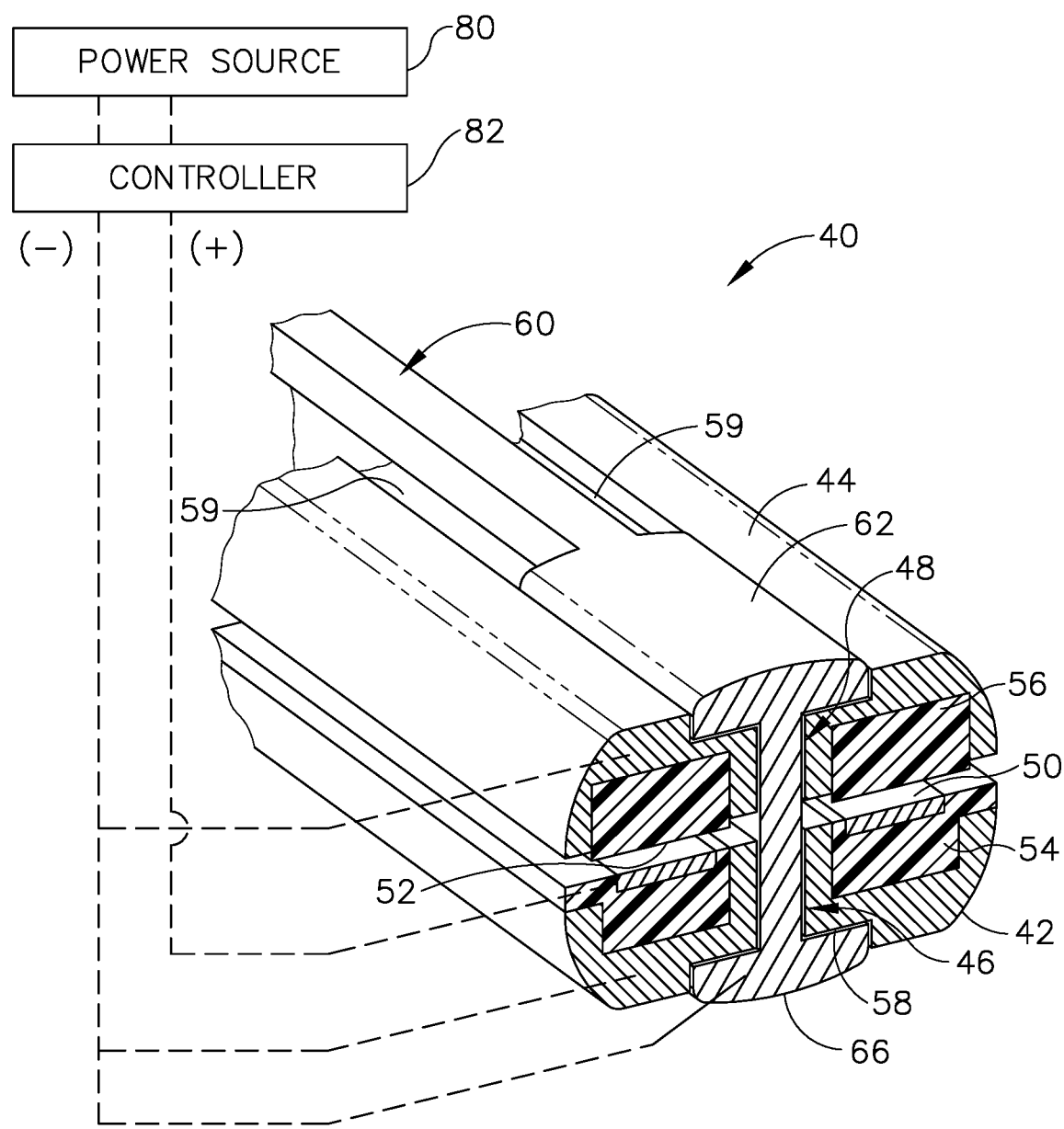
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22).

With tissue layers captured between jaws (42, 44) firing beam (60) continues to advance distally by the user squeezing trigger (24) toward pistol grip (22). As firing beam (60) advances distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52).

While several of the teachings below are described as variations to electrosurgical instrument (10), it should be understood that various teachings below may also be incorporated into various other types of devices. By way of example only, in addition to being readily incorporated into electrosurgical instrument (10), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

II. Exemplary Articulation Joint Configurations

As noted above, some versions of shaft (30) include an articulation section (36), which is operable to selectively position end effector (40) at various angles relative to the longitudinal axis defined by sheath (32). Several examples of forms that articulation section (36) and other components of shaft (30) may take will be described in greater detail below, while further examples will be apparent to those of ordinary skill in the art in view of the teachings herein. By way of example only, some merely illustrative alternative examples of articulation section (36) are disclosed in U.S. patent application Ser. No. 13/235,683, entitled "Articulation Joint Features for Articulating Surgical Device," filed on Sep. 19, 2011 and issued as U.S. Pat. No. 9,220,559 on Dec. 29, 2015, the disclosure of which is incorporated by reference herein.

A. Exemplary Articulation Section with Parallel Support Rails

Figure 5:
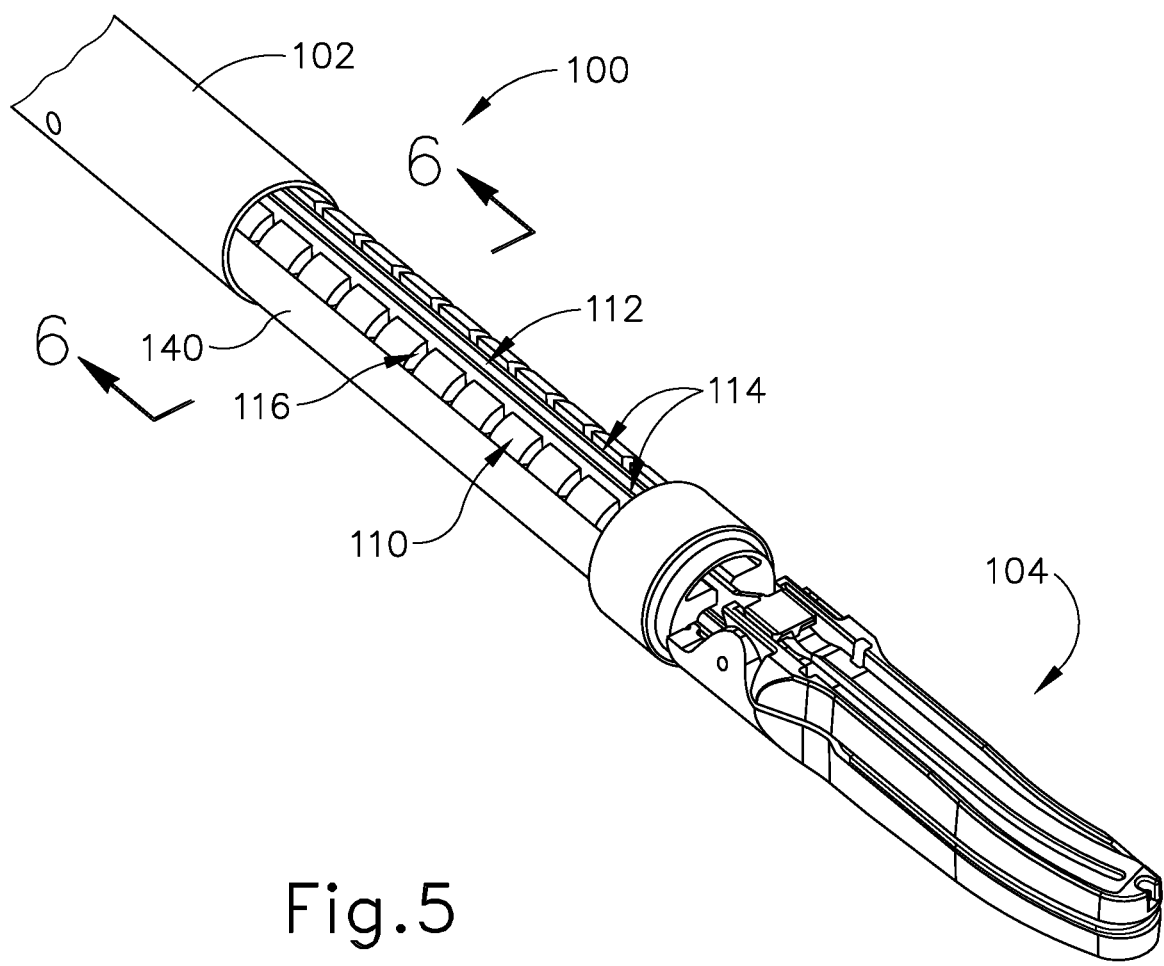
FIG. 5 depicts a perspective view of an exemplary articulation section for the shaft of the device of FIG. 1.
Figure 6:
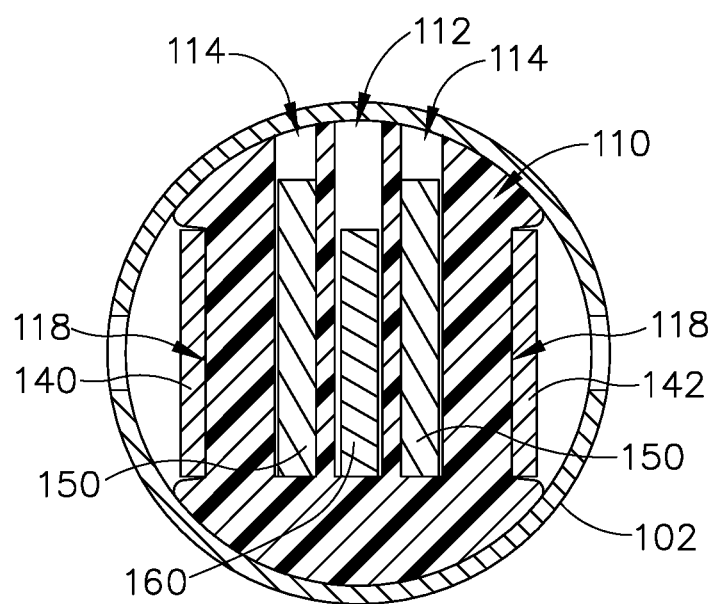
FIG. 6 depicts a cross-sectional end view of the articulation section of FIG. 5, taken along line 6-6 of FIG. 5.

FIGS. 5-6 show an exemplary articulation section (100) disposed between a rigid shaft section (102) and an end effector (104). It should be understood that these features may be readily incorporated into electrosurgical instrument (10) described above, with shaft section (102) corresponding to shaft (30) and end effector (104) corresponding to end effector (40). Articulation section (100) of this example comprises a molded member (110) that defines a plurality of slots (112, 114, 116) and a pair of recesses (118). Molded member (110) may comprise a variety of materials, including but not limited to Vectra, Isoplast, a high density polyethylene, and/or various other materials. In some instances, the material forming molded member (110) provides a resilient bias to molded member (110) to assume a substantially straight orientation. Other suitable selections and properties for molded member (110) will be apparent to those of ordinary skill in the art in view of the teachings herein. Similarly, while molded member (110) is formed through a molding process in the present example, it should be understood that a variety of other processes may be used, including but not limited to extrusion, etc.

Slots (112, 114) extend longitudinally along the length of molded member (110), opening at a top portion of molded member (110) but terminating within the bottom portion of molded member (110). Slot (112) extends along the axis of molded member (110) while slots (114) are laterally offset from the axis. Slots (116) are oriented transversely relative to the axis of molded member (110). Like slots (112, 114), slots (116) also open at a top portion of molded member (110) while terminating within the bottom portion of molded member (110). Slots (116) are configured to facilitate flexing of molded member (110). Slot (112) is configured to slidingly receive firing beam (160). Firing beam (160) is equivalent to firing beam (60) discussed above. It should therefore be understood that firing beam (160) is operable to translate longitudinally within slot (112). It should also be understood that firing beam (160) has sufficient flexibility to enable firing beam to translate along a curved path when articulation section is in a bent, articulated configuration. The material forming molded member (110) and/or coatings on molded member (110) may be selected to minimize friction between firing beam (160) and molded member (110). By way of example only, molded member (110) may include baked on silicone and/or sodium stearate and/or various other materials.

Recesses (118) are configured to receive articulation bands (140, 142). The distal ends of articulation bands (140, 142) are secured to the distal end of articulation section (100). The proximal ends of articulation bands (140, 142) are in communication with a control such as articulation control (28). In some versions, articulation control (28) is operable to selectively advance or retract one band (140, 142) while keeping the position of the other band (140, 142) substantially constant, thereby causing articulation section (100) to bend. In some other versions, articulation control (28) is operable to selectively advance band (140) while simultaneously retracting band (142); and/or to selectively retract band (140) while simultaneously advancing band (142). Of course, bands (140, 142) may be substituted with cables and/or various other types of components. A flexible sheath or wrap may be positioned about articulation section (100), to assist in holding bands (140, 142) against molded member (110). In addition or in the alternative, molded member (110) may include vertically extending slots and/or other types of features that hold bands (140, 142) against molded member (110), including when articulation section (100) is in a bent configuration.

Slots (114) are configured to receive spring beams (150). In some versions, spring beams (150) are resiliently biased to orient molded member (110) in a substantially straight configuration. This resilient bias may also reduce binding loads on firing beam (160) when firing beam (160) translates through articulation section (100) in a bent configuration. Spring beams (150) are also configured to enhance the structural integrity of articulation section (100), such as by providing resistance to lateral buckling or blowout of firing beam (160) when firing beam (160) translates through articulation section (100) in a bent configuration. Since spring beams (150) are located in slots (114) that are separate from the slot (112) for firing beam (160), spring beams (150) do not come into contact with firing beam (160) during operation of articulation section (100) and/or during operation of firing beam (160). This spacing may also reduce pinch loads of spring beams (150) on firing beam (160).

In some versions, both ends of each spring beam (150) are unsecured to anything, such that spring beams (150) float freely within articulation section (100). In some other versions, one end of each spring beam (150) is secured relative to articulation section (100) while the other end of each spring beam (150) floats freely. Other suitable components, configurations, arrangements, and relationships will be apparent to those of ordinary skill in the art in view of the teachings herein. It should also be understood that any of slots (112, 114, 116) and/or some other component of articulation section (110) may accommodate one or more wires that provide electrical communication between end effector (104) and a power source.

B. Exemplary Articulation Section Formed by Molded Joint

Figure 7:
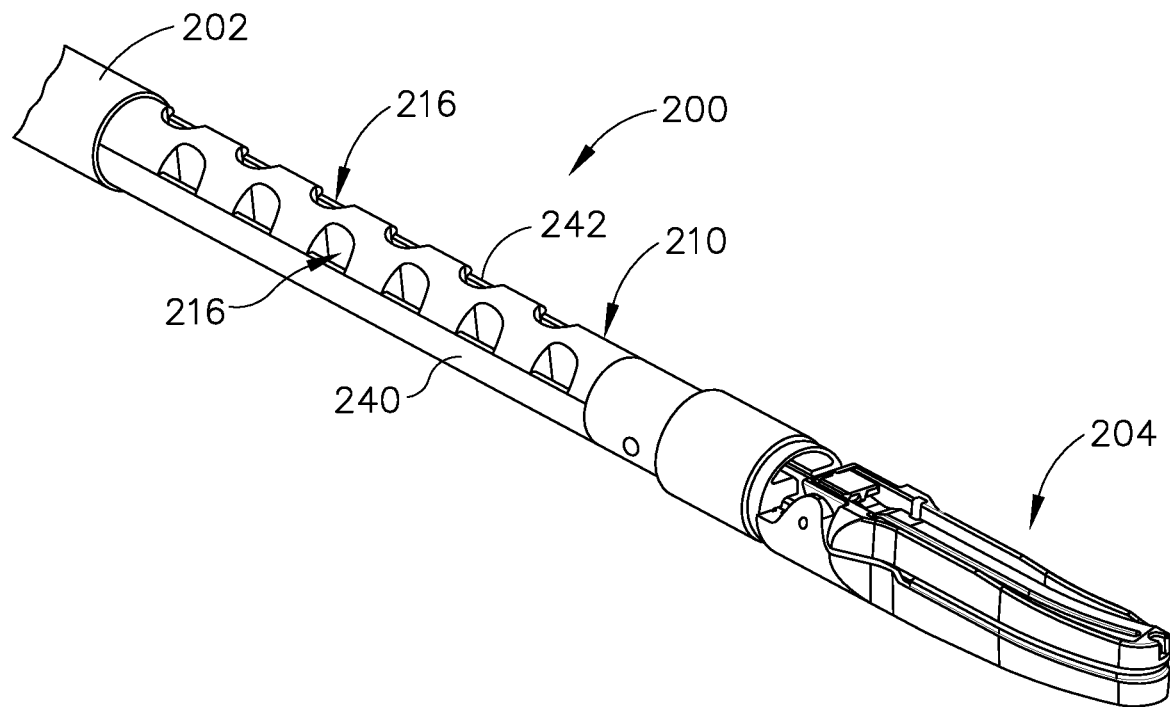
FIG. 7 depicts a top perspective view of another exemplary articulation section for the shaft of the device of FIG. 1.
Figure 8:
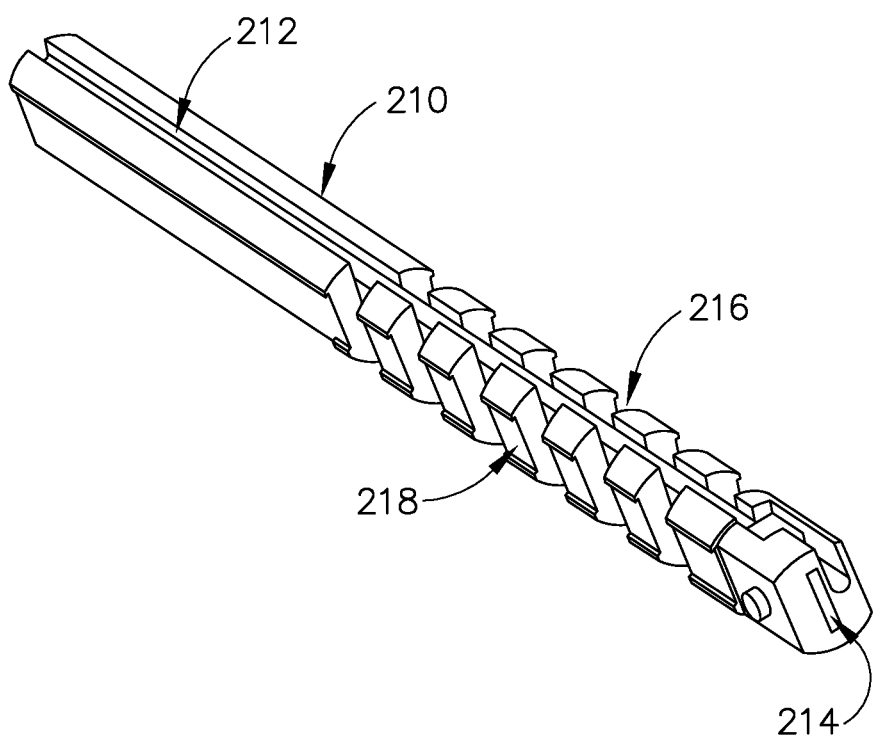
FIG. 8 depicts a bottom perspective view of the articulation section of FIG. 7.
Figure 9:
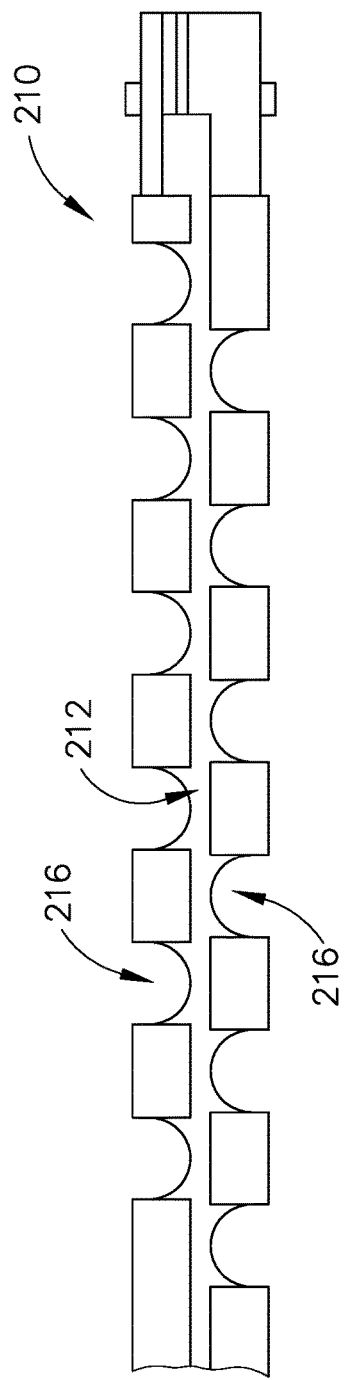
FIG. 9 depicts a top plan view of the articulation section of FIG. 7.

FIGS. 7-9 show another exemplary articulation section (200) disposed between a rigid shaft section (202) and an end effector (204). It should be understood that these features may be readily incorporated into electrosurgical instrument (10) described above, with shaft section (202) corresponding to shaft (30) and end effector (204) corresponding to end effector (40). Articulation section (200) of this example comprises a molded member (210) that defines a plurality of slots (212, 216), a lumen (214), and a pair of recesses (218). Molded member (210) may comprise a variety of materials, including but not limited to Vectra, Isoplast, a high density polyethylene, and/or various other materials. In some instances, the material forming molded member (210) provides a resilient bias to molded member (210) to assume a substantially straight orientation. Other suitable selections and properties for molded member (210) will be apparent to those of ordinary skill in the art in view of the teachings herein. Similarly, while molded member (210) is formed through a molding process in the present example, it should be understood that a variety of other processes may be used.

As best seen in FIGS. 8-9, slot (212) and lumen (214) each extend longitudinally along the length of molded member (110). Slot (212) is configured to accommodate one or more wires that provide electrical communication between end effector (204) and a power source. Lumen (214) is configured to slidingly receive a firing beam (not shown), much like slot (112) receiving firing beam (160) as described above. Thus, a firing beam may translate through molded member (210) regardless of whether articulation section (200) is in a substantially straight or bent configuration. Slots (216) are oriented transversely relative to the axis of molded member (210). Slots (216) are configured to facilitate flexing of molded member (210). In the present examples, as best seen in FIG. 9, slots (216) are alternatingly staggered in their relative spacing along the length of molded member (210). Such a configuration may facilitate bending of molded member (210). In some other versions, slots (216) are opposingly positioned instead of being staggered.

Recesses (218) are configured to receive articulation bands (240, 242). The distal ends of articulation bands (240, 242) are secured to the distal end of articulation section (200). The proximal ends of articulation bands (240, 242) are in communication with a control such as articulation control (28). In some versions, articulation control (28) is operable to selectively advance or retract one band (240, 242) while keeping the position of the other band (240, 242) substantially constant, thereby causing articulation section (200) to bend. In some other versions, articulation control (28) is operable to selectively advance band (240) while simultaneously retracting band (242); and/or to selectively retract band (240) while simultaneously advancing band (242). As yet another merely illustrative example, articulation control (28) may be operable to selectively advance band (240) while letting band (242) remain slack/free; and/or to selectively retract band (240) while letting band (242) remain slack/free. Of course, bands (240, 242) may be substituted with cables and/or various other types of components; and may be operable in various other ways.

A flexible sheath or wrap may be positioned about articulation section (200), to assist in holding bands (240, 242) against molded member (210). In addition or in the alternative, molded member (210) may include vertically extending slots and/or other types of features that hold bands (240, 242) against molded member (210), including when articulation section (200) is in a bent configuration.

Figure 10:
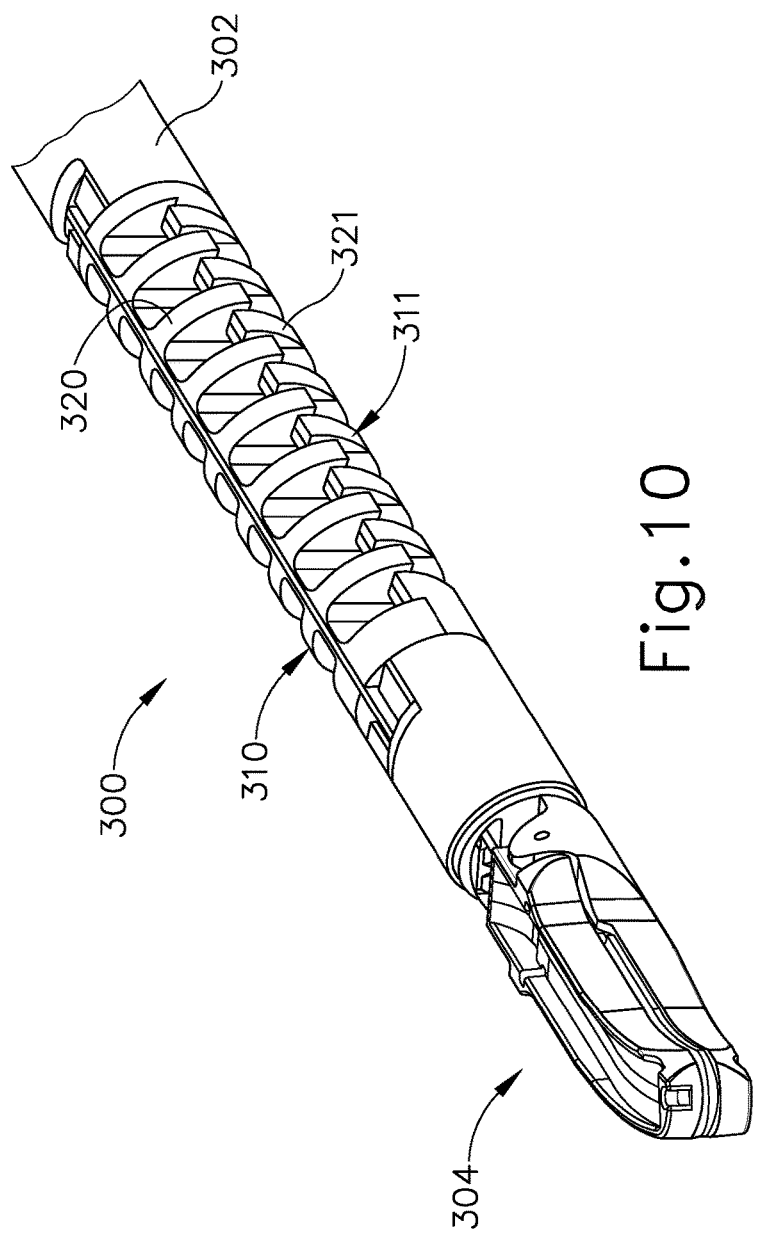
FIG. 10 depicts a perspective view of another exemplary articulation section for the shaft of the device of FIG. 1.
Figure 11:
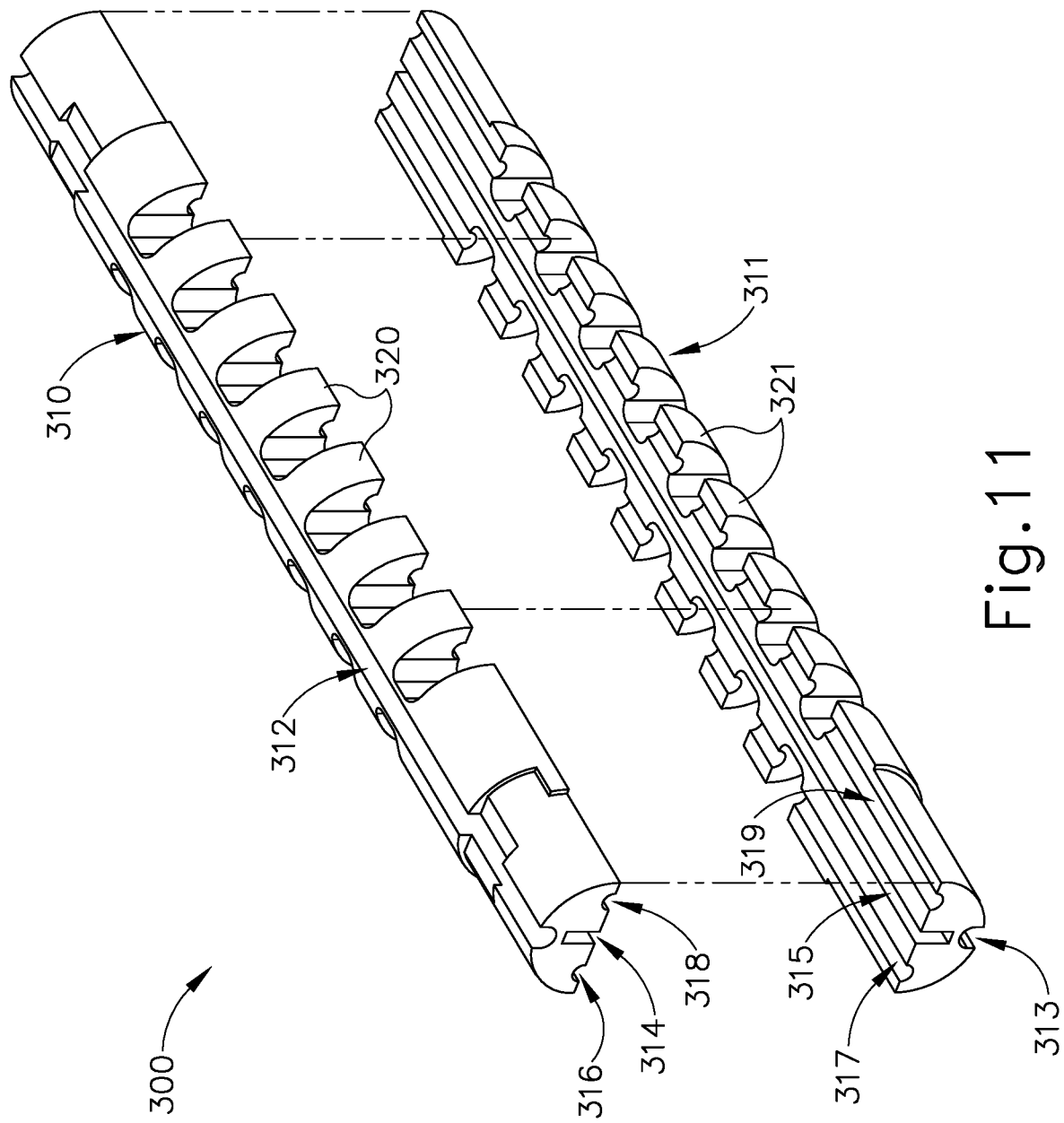
FIG. 11 depicts an exploded view of the articulation section of FIG. 10.

FIGS. 10-11 show another exemplary articulation section (300) disposed between a rigid shaft section (302) and an end effector (304). It should be understood that these features may be readily incorporated into electrosurgical instrument (10) described above, with shaft section (302) corresponding to shaft (30) and end effector (304) corresponding to end effector (40). Articulation section (300) of this example comprises a pair of molded members (310, 311). Each molded member (310, 311) may comprise a variety of materials, including but not limited to Vectra, Isoplast, a high density polyethylene, and/or various other materials. In some instances, the material forming molded members (310, 311) provides a resilient bias to molded members (310, 311) to assume a substantially straight orientation. Other suitable selections and properties for molded members (310, 311) will be apparent to those of ordinary skill in the art in view of the teachings herein. Similarly, while molded members (310, 311) are formed through a molding process in the present example, it should be understood that a variety of other processes may be used. Molded members (310, 311) are configured to apposingly join together to form articulation section (300), as shown in FIG. 10. Molded members (310, 311) may be secured together in numerous ways, including but not limited to adhesives, ultrasonic welding, snap-fittings, clamps, clips, an external sheath, etc.

As best seen in FIG. 11, molded member (310) includes a plurality of recesses (312, 314, 316, 318) and a plurality of ribs (320). Recesses (312, 314, 316, 318) all extend longitudinally along the length of molded member (310). Recess (312) is positioned on an upper side of molded member (310) while recesses (314, 316, 318) are positioned on a lower side of molded member (310). Ribs (320) extend laterally from molded member (310) and are spaced apart equidistantly along the length of molded member. Recess (312) is configured to accommodate one or more wires that provide electrical communication between end effector (304) and a power source.

Molded member (311) also includes a plurality of recesses (313, 315, 317, 319) and a plurality of ribs (321). Recesses (313, 315, 317, 319) all extend longitudinally along the length of molded member (311). Recess (313) is positioned on an upper side of molded member (311) while recesses (315, 317, 319) are positioned on a lower side of molded member (311). Ribs (321) extend laterally from molded member (310) and are spaced apart equidistantly along the length of molded member. Recess (313) is configured to accommodate one or more wires that provide electrical communication between end effector (304) and a power source. In some versions, either recess (312) or recess (313) receives such a wire while the other recess (312, 313) does not receive a wire. In some other versions, each recess (312, 313) receives at least one respective wire.

When molded members (310, 311) are joined together as shown in FIG. 10, recesses (314, 315) align and cooperate to form a channel through which a firing beam (not shown) may be slidably disposed. This channel is thus functionally similar to lumen (214) described above. In addition, recesses (316, 317) align and cooperate to form a channel to receive a first articulation cable (not shown) while recesses (318, 319) align and cooperate to form a channel to receive a second articulation cable (not shown) when molded members (310, 311) are joined together. Such articulation cables may be operable in a manner similar to that described above for articulation bands (140, 142). In some other versions, recesses (316, 317, 318, 319) are configured to form channels that receive bands instead of cables. Other suitable features that may be used to provide articulation of articulation section (300) will be apparent to those of ordinary skill in the art in view of the teachings herein. As best seen in FIG. 10, ribs (320, 321) are configured to interleave with each other when molded members (310, 311) are joined together. However, it should be understood that ribs (320, 321) may instead align with each other, if desired. It should also be understood that ribs (320, 321) permit articulation section (300) to bend relative to its longitudinal axis regardless of whether ribs (320, 321) are aligned or interleaved. In some versions, an outer wrap or shrink tubing is provided about the exterior of molded members (310, 311), though this is merely optional. Such a wrap or tubing may assist in holding molded members (310, 311) together.

Figure 12:
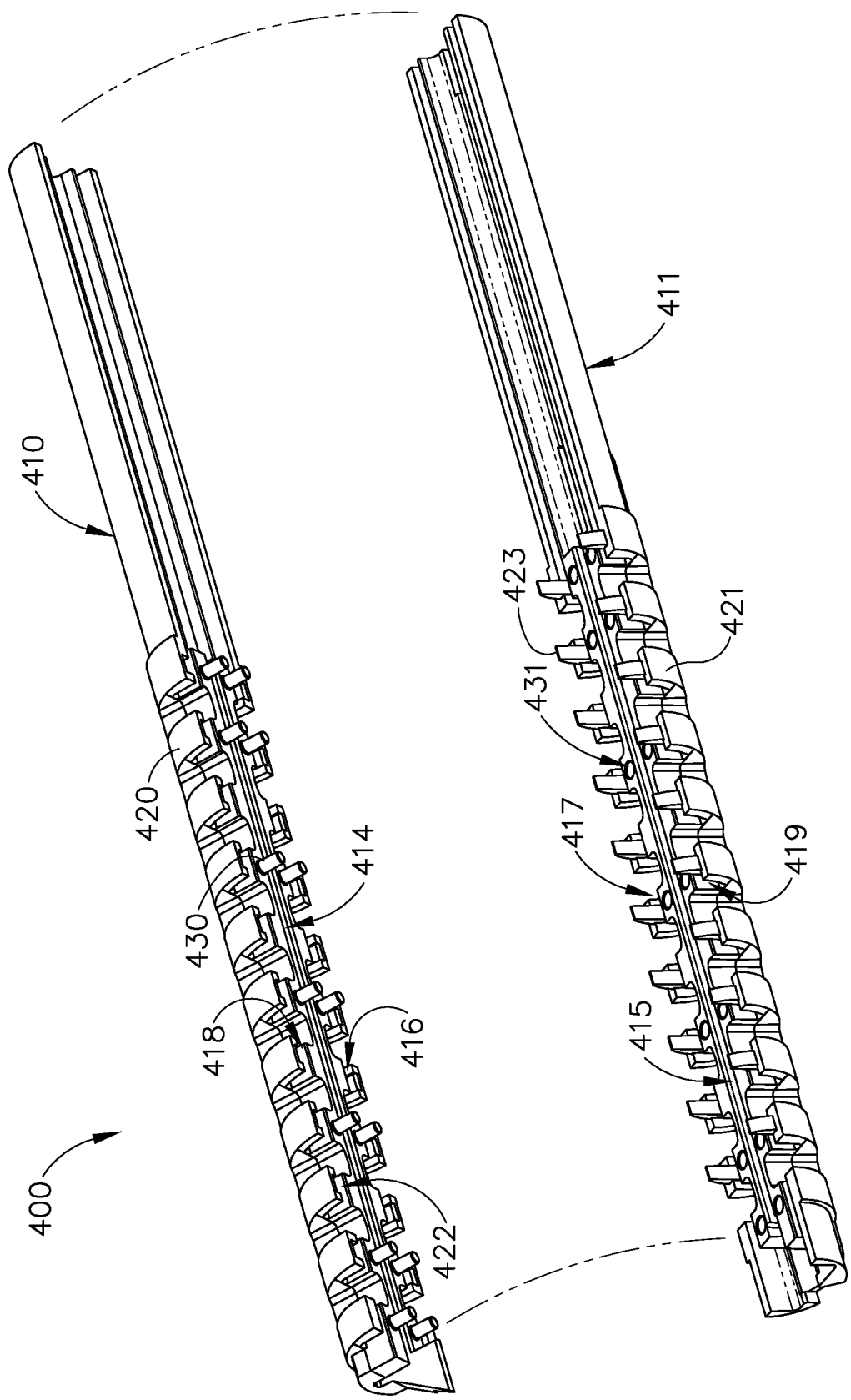
FIG. 12 depicts an exploded view of another articulation section for the shaft of the device of FIG. 1.
Figure 13:
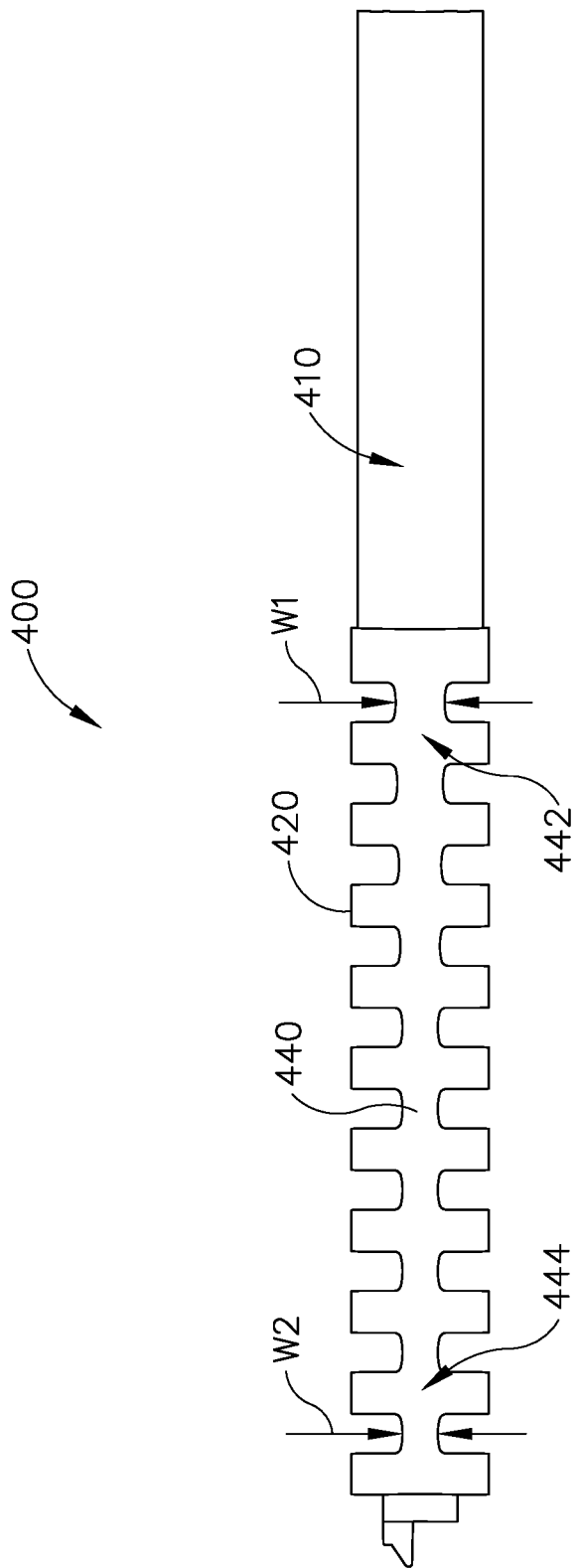
FIG. 13 depicts a plan view of the articulation section of FIG. 12.
Figure 14:
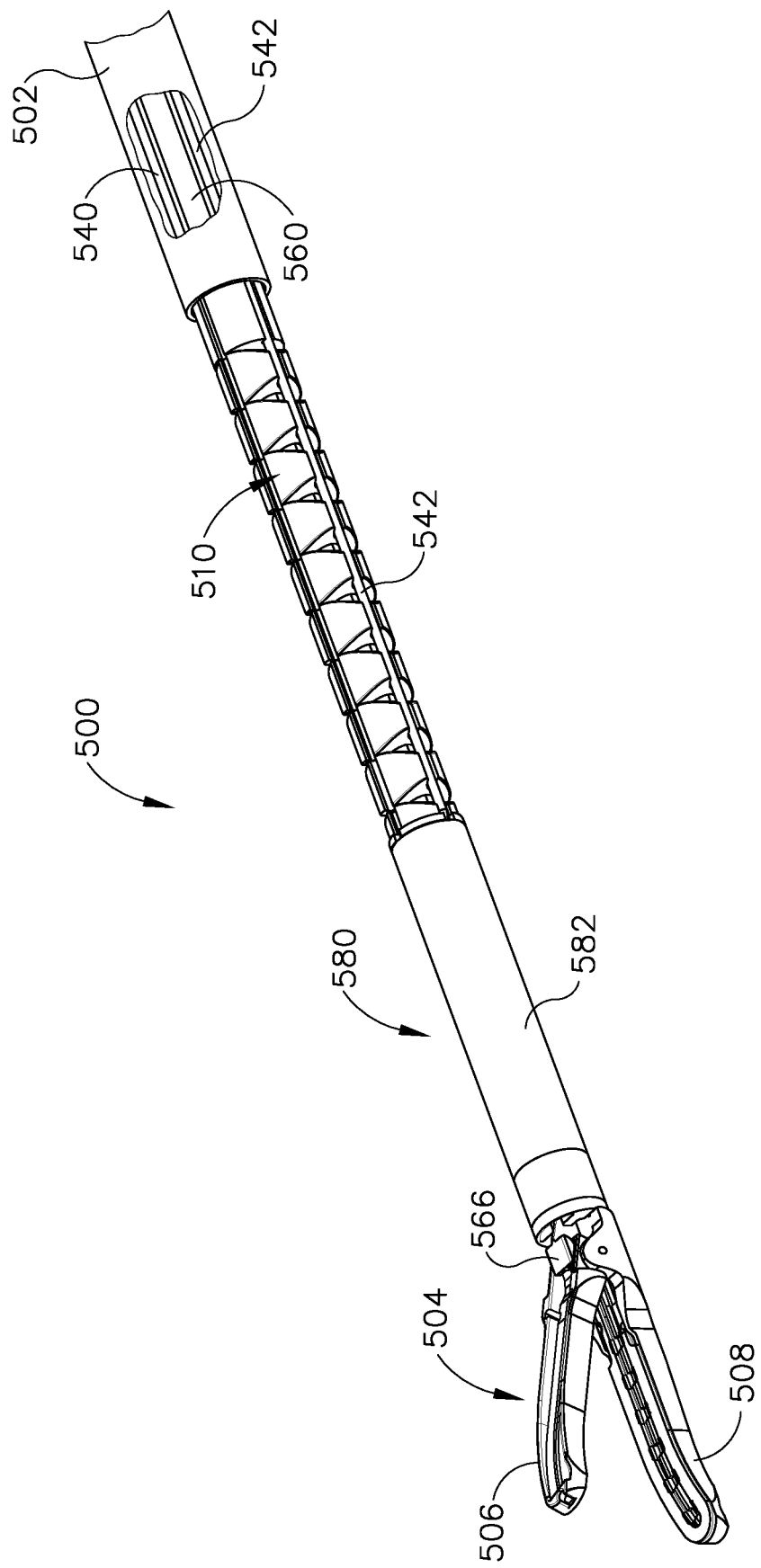
FIG. 14 depicts a perspective view of another exemplary articulation section for the shaft of the device of FIG. 1.

FIGS. 12-13 show yet another exemplary articulation section (400) that is essentially a variation of articulation section (300) described above. Articulation section (400) is formed by a pair of apposed molded members (410, 411). Each molded member (410, 411) may comprise a variety of materials, including but not limited to Vectra, Isoplast, a high density polyethylene, and/or various other materials. In some instances, the material forming molded members (410, 411) has resilient properties and thereby biases molded members (410, 411) to assume a substantially straight orientation. In other words, molded members (410, 411) may have shape memory providing a bias to a substantially straight configuration. Other suitable selections and properties for molded members (410, 411) will be apparent to those of ordinary skill in the art in view of the teachings herein. Similarly, while molded members (410, 411) are formed through a molding process in the present example, it should be understood that a variety of other processes may be used.

Molded member (410) includes a plurality of recesses (414, 416, 418) and a plurality of ribs (420). Recesses (414, 416, 418) are essentially equivalent to recesses (314, 316, 318) described above, such that they will not be described in greater detail here. It should also be understood that molded member (410) may include a recess that is analogous to recess (312) described above. Likewise, molded member (411) includes a plurality of recesses (415, 417, 419) and a plurality of ribs (421), with recesses (415, 417, 419) being essentially equivalent to recesses (315, 317, 319) described above. Molded member (411) may also include a recess that is analogous to recess (313) described above.

Unlike molded member (310), molded member (410) includes a plurality of posts (430) extending downwardly from the underside of molded member (410). Ribs (420) of molded member (410) also include a plurality of recesses (422). Unlike molded member (311), molded member (411) includes a plurality of openings (431) that are configured to receive posts (430) when molded members (410, 411) are joined together. Ribs (421) of molded member (411) include a plurality of protrusions (423), which are received in recesses (422) of corresponding ribs (420) of molded member (410) when molded members (410, 411) are joined together. Thus, unlike ribs (320, 321) of molded members (310, 311), ribs (420, 421) align with each other when molded members (410, 411) are joined together.

FIG. 13 illustrates another difference between molded members (410, 411) and molded members (310, 311). In particular, FIG. 13 shows how the thickness of a flexible feature in the form of a spine section (440) of molded members (410, 411) decreases along the length of articulation section (400). It should be understood that the left-hand side of FIG. 13 corresponds with the distal end of articulation section (400) while the right-hand side of FIG. 13 corresponds with the proximal end of articulation section (400). As shown, a proximal region (442) of spine section (440) has a width "W1" that is greater than the width "W2" of a distal region (444) of spine section (440). Such a configuration may reduce the amount of force necessary to bend the distal end of articulation section (400) relative to the longitudinal axis defined by articulation section (400). In other words, gradually reducing the width of spine section (440) along length of articulation section (400) may facilitate articulation of articulation section (400). Of course, any other suitable features or configurations may be used. In some versions, an outer wrap or shrink tubing is provided about the exterior of molded members (410, 411), though this is merely optional. Such a wrap or tubing may assist in holding molded members (410, 411) together.

C. Exemplary Beaded Articulation Section

Figure 15:
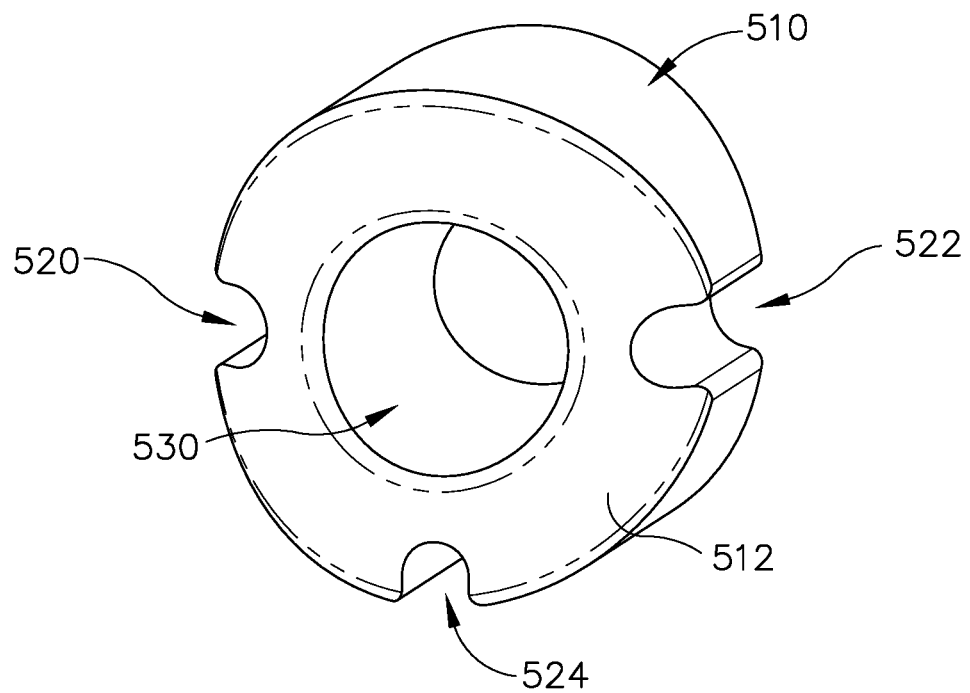
FIG. 15 depicts a perspective view of a bead component of the articulation section of FIG. 14.
Figure 16:
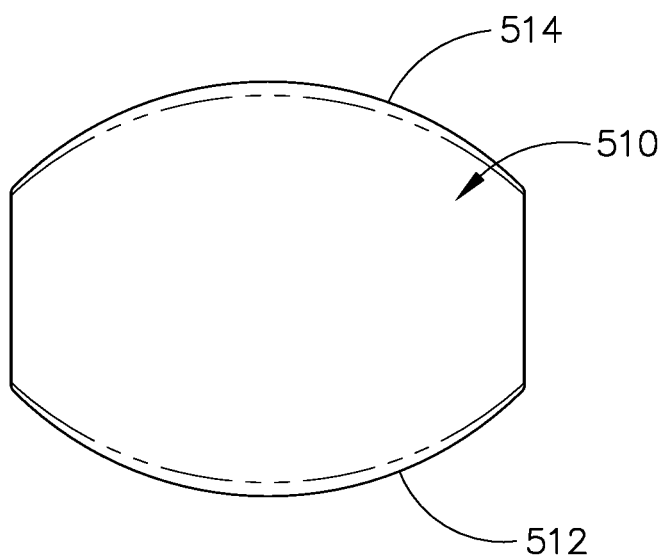
FIG. 16 depicts a top plan view of the bead component of FIG. 15.

FIGS. 14-20 show yet another exemplary articulation section (500) that is disposed between a rigid shaft section (502) and an end effector (504). As will be described in greater detail below, end effector (504) is coupled with a rotation section (580), which is positioned distal to articulation section (500). It should be understood that these features may be readily incorporated into electrosurgical instrument (10) described above, with shaft section (502) corresponding to shaft (30) and end effector (504) corresponding to end effector (40). However, as will be described in greater detail below, in some versions end effector (504) is rotatable relative to shaft section (502) and relative to articulation section (500). Articulation section (500) of this example comprises a plurality of coaxially aligned beads (510). As best seen in FIGS. 15-16, each bead (510) includes a first face (512) and a second face (514). Each face (512, 514) has a convex configuration. With beads (510) positioned adjacent to each other, the convex configuration of faces (512, 514) may facilitate articulation of articulation section (520). For instance, the face (512) of one bead (510) may simply roll against the face (514) of an adjacent bead (510) during articulation.

Figure 19:
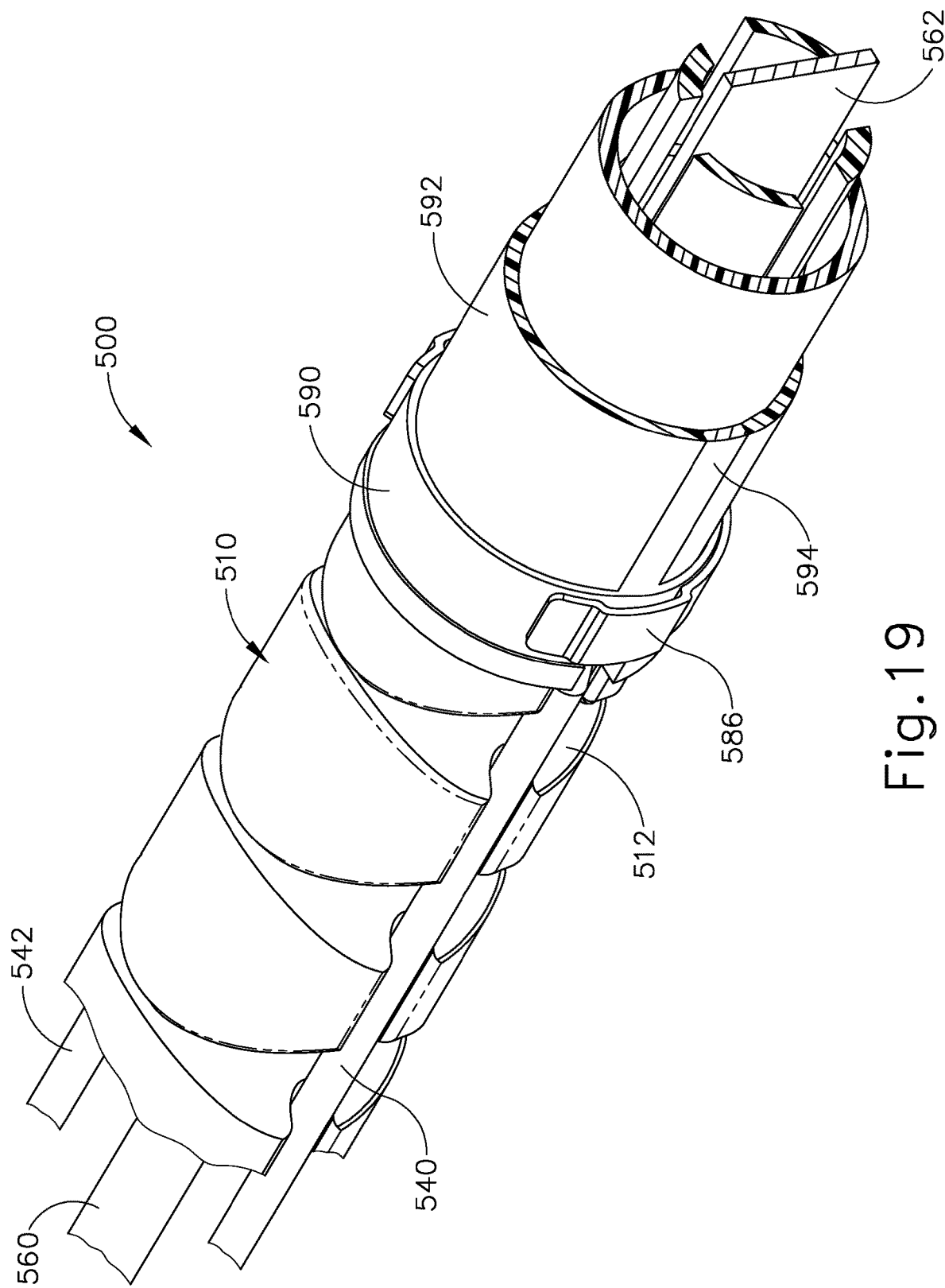
FIG. 19 depicts a partial perspective view of an upper portion of a distal rotation feature associated with the articulation section of FIG. 14.
Figure 20:
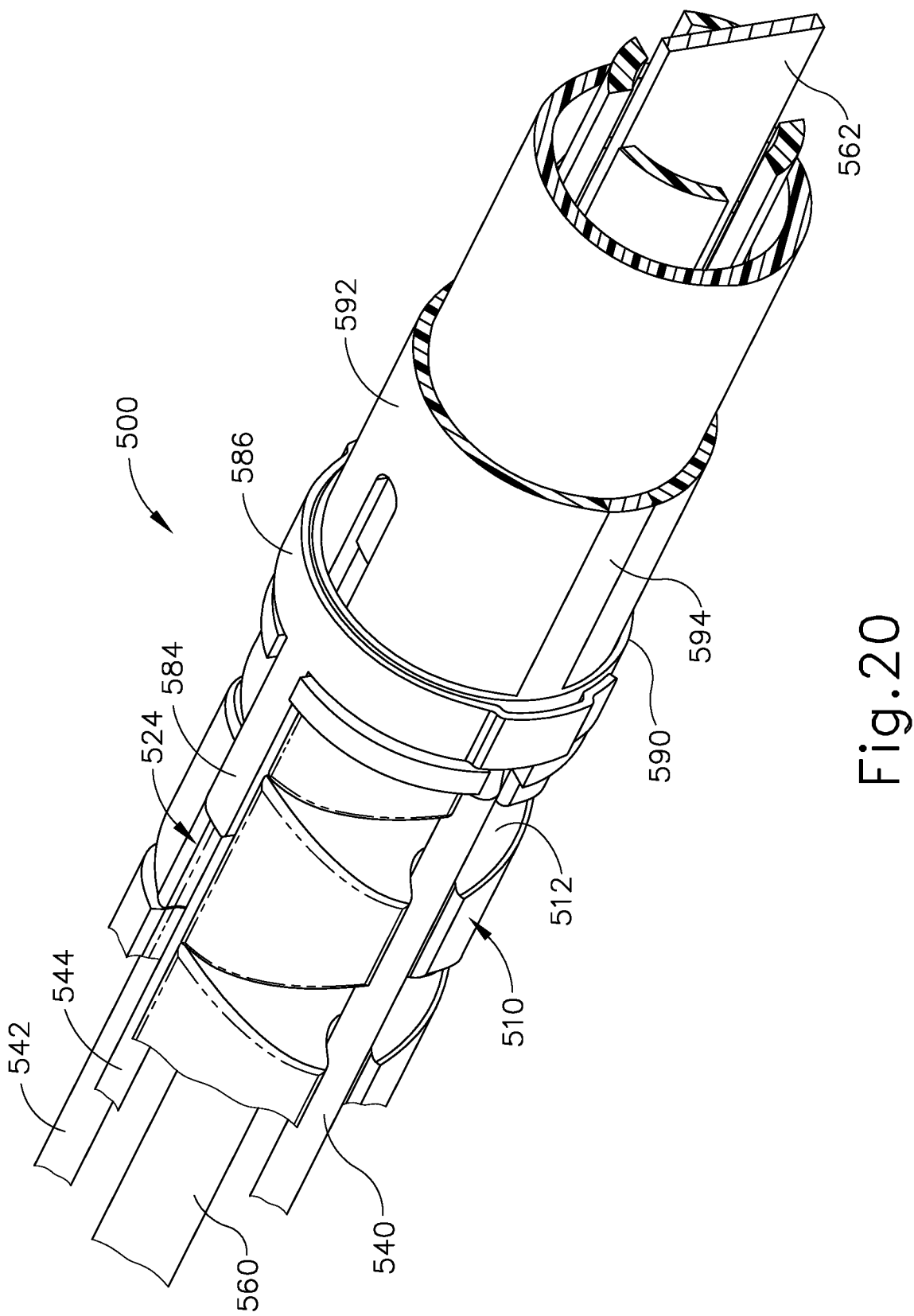
FIG. 20 depicts a partial perspective view of a lower portion of the distal rotation feature of FIG. 19.

The outer perimeter of each bead (510) also includes recesses (520, 522, 524) extending from face (512) to face (514). Beads (510) are all configured similarly in this example, such that corresponding recesses (520, 522, 524) of adjacent beads (510) may be readily aligned with each other. As shown in FIGS. 14 and 18-20, recesses (520, 522) receive respective articulation cables (540, 542). Articulation cables (540, 542) are operable in a manner similar to that described above for articulation bands (140, 142). Of course, cables (540, 542) may be substituted with bands and/or various other kinds of structures. Recess (524) is configured to receive a wire (544), as shown in FIG. 20. As will be described in greater detail below, wire (544) is configured to provide electrical communication between end effector (504) and a power source. It should be understood that, as with other wires referred to herein, wire (544) may readily bend with articulation section (500) when articulation section (500) is articulated.

Figure 17:
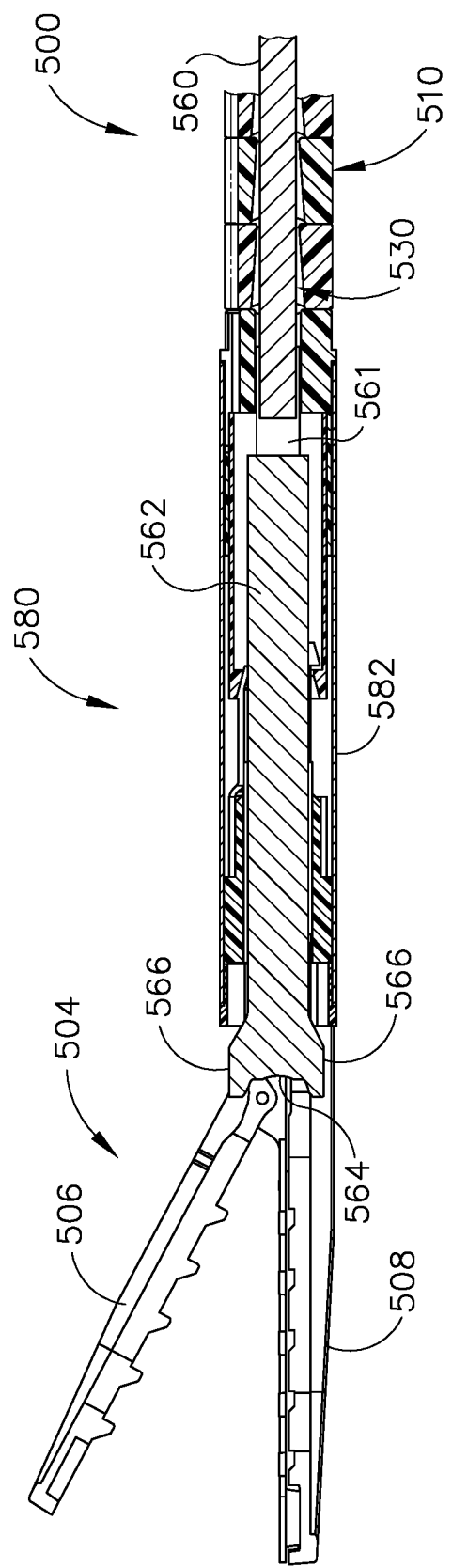
FIG. 17 depicts a cross-sectional side view of the articulation section of FIG. 14.
Figure 18:
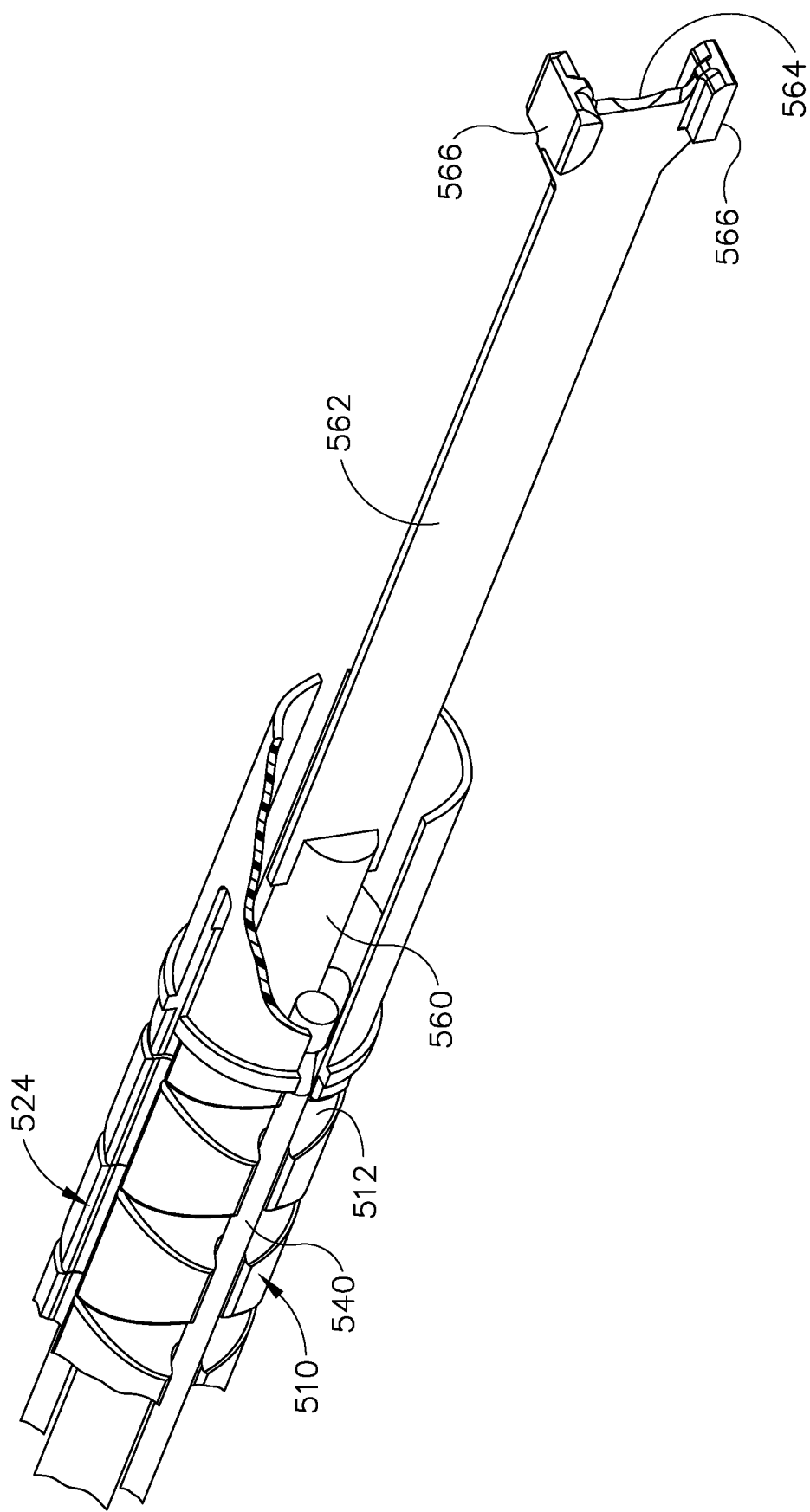
FIG. 18 depicts a partial perspective view of distal end portions of the articulation section of FIG. 14.

Each bead (510) further includes a central bore (530) extending from face (512) to face (514). Bores (530) of all beads (510) are all substantially coaxially aligned when articulation section (500) is in a substantially straight configuration. As best seen in FIG. 17, a firing drive cable (560) extends through bores (530). Drive cable (560) of the present example comprises a multi-strand construction with sufficient tensile strength to support distal and proximal driving forces through drive cable (560). The construction of drive cable (560) also permits drive cable (560) to be used to rotatably drive end effector (504) in either direction as will be described in greater detail below. As also best seen in FIG. 17, each bore (530) has a tapered configuration, which may facilitate flexing of drive cable (560) through articulation section (500) when articulation section (500) is in an articulated configuration. Bores (530) are also sized to permit rotation of drive cable (560) within beads (510), as will be described in greater detail below. In some versions, an outer wrap or shrink tubing is provided about the exterior of beads (510), though this is merely optional. Such a wrap or tubing may assist in holding beads (510) together.

Drive cable (560) is secured to a firing bar (562) via an adapter (561) in a region distal to articulation section (500). Firing bar (562) is essentially equivalent to firing bar (60) described above. In particular, firing bar (562) includes a distal blade (564) and a pair of flanges (566) that are configured to close jaws (506, 508) when firing bar (562) is advanced distally; and to open jaws (506, 508) when firing bar (562) is retracted proximally. Drive cable (560) is operable to drive firing bar (562) distally and proximally by translating drive cable (560) distally or proximally. Drive cable (560) may be translated by actuation of trigger (24) and/or in any other suitable fashion.

Other suitable components, features, configurations, and operabilities for the above described articulation sections (100, 200, 300, 400, 500) will be apparent to those of ordinary skill in the art in view of the teachings herein.

III. Exemplary Articulation Control Configurations

Articulation control (28) may take a variety of forms. By way of example only, articulation control (28) may be configured in accordance with one or more teachings of U.S. patent application Ser. No. 13/235,623, entitled "Control Features for Articulating Surgical Device," filed on Sep. 19, 2011 and issued as U.S. Pat. No. 9,877,720 on Jan. 30, 2018, the disclosure of which is incorporated by reference herein. As another merely illustrative example, articulation control (28) may be configured in accordance with one or more teachings of U.S. patent application Ser. No. 13/235,648, entitled "Control Features for Articulating Surgical Device," filed on Sep. 19, 2011, now abandoned, the disclosure of which is incorporated by reference herein. Furthermore, articulation section may be configured in accordance with the teachings of at least one other of the references cited herein. Various other suitable forms that articulation control (28) may take will be apparent to those of ordinary skill in the art in view of the teachings herein.

IV. Other Exemplary Features

It should be understood that any of the versions of electrosurgical instrument (10) described herein may include various other features in addition to or in lieu of those described above. By way of example only, FIGS. 14 and 17-20 show an example of a distal rotation section (580) that may be used to provide rotatability of end effector (504) in a region that is distal to articulation section (500). In other words, rotation section (580) and end effector (504) may be rotated together while articulation section (500) and shaft section (502) remain substantially stationary. It should be understood that rotation section (580) and end effector (504) may be rotated together regardless of whether articulation section (500) is in a substantially straight configuration or a bent/articulated configuration.

In the present example, rotation section (580) and end effector (504) are rotated by rotating drive cable (560). For instance, in some versions, handpiece (20) includes a knob or other feature that is operable to rotate drive cable (560). In some other versions, handpiece (20) is omitted, and rotation section (580) and end effector (504) are driven by motor, solenoid, and/or some other feature, as part of a robotic system. Other suitable components, configurations, and techniques for driving rotation system and end effector (504) will be apparent to those of ordinary skill in the art in view of the teachings herein. It should also be understood that an electrosurgical instrument (10) may provide both of two forms of rotation. For instance, one form of rotation may include simultaneous rotation of shaft section (502), articulation section (500), rotation section (580), and end effector (504) (regardless of whether articulation section (500) is in a straight or bent configuration); while another form of rotation may include rotation of only rotation section (580) and end effector (504), with shaft section (502) and articulation section (500) remaining rotationally stationary (again regardless of whether articulation section (500) is in a straight or bent configuration).

As noted above, wire (544) passes through articulation section (500) to provide electrical communication between end effector (504) and a power source that is proximal to shaft (502). In some the present example, rotation section (580) is configured to permit electrical power to be communicated from wire (544) to end effector (504) without wire (544) getting wrapped or twisted when end effector (504) is rotated relative to articulation section (500). In particular, and as best seen in FIGS. 19-20, wire (544) is secured to a prong (584) of a slip ring (586). Slip ring (586) is positioned and resiliently biased to contact a cuff (590), which includes distally extending arms (594). Prong (584), slip ring (586), cuff (590), and extending arms (594) each comprise an electrically conductive material. These components are all contained within a sheath (582). Arms (594) are in electrical communication with one or both of jaws (506, 508), to provide bipolar RF energy through either or both jaws (506, 508) as described above and as described in various references that are cited herein.

Cuff (590) is secured to a body (592) within rotation section (580). Cuff (590) and body (592) rotate together with end effector (504). The relationship between slip ring (586) and cuff (590) provides electrical continuity between slip ring (586) and cuff (590) even as cuff (590) rotates with end effector (504) while slip ring (586) and articulation section (500) remain rotationally stationary. It should be understood that one or more bearing surfaces or features may also be provided between articulation section (500) and rotation section (580) to further facilitate rotation of rotation section (580) relative to articulation section (580).

While the example shown in FIGS. 14 and 17-20 is provided in the context of articulation section (500), it should be understood that rotation section (580) may also be readily incorporated into any of the other versions of articulation sections or electrosurgical instrument (10) described herein. It should also be understood that rotation section (580) may be readily incorporated into to various other kinds of instruments as well, including but not limited to the various kinds of instruments that are described herein and/or that are described in the various references that are cited herein. Still other suitable instruments in which rotation section (580) may be incorporated will be apparent to those of ordinary skill in the art in view of the teachings herein.

It should be understood that any of the devices herein may also include one or more of the various features disclosed in U.S. patent application Ser. No. 13/235,623, entitled "Control Features for Articulating Surgical Device," filed on Sep. 19, 2011 and issued as U.S. Pat. No. 9,877,720 on Jan. 30, 2018, the disclosure of which is incorporated by reference herein; U.S. patent application Ser. No. 13/235,648, entitled "Control Features for Articulating Surgical Device," filed on Sep. 19, 2011 and published as U.S. Patent Pub. No. 2012/0078244, now abandoned, the disclosure of which is incorporated by reference herein; and/or U.S. patent application Ser. No. 13/235,683, entitled "Control Features for Articulating Surgical Device," filed on Sep. 19, 2011 and issued as U.S. Pat. No. 9,220,559 on Dec. 29, 2015, the disclosure of which is incorporated by reference herein.

It should also be understood that any of the devices described herein may be modified to include a motor or other electrically powered device to drive an otherwise manually moved component. Various examples of such modifications are described in U.S. patent application Ser. No. 13/151,481, entitled "Motor Driven Electrosurgical Device with Mechanical and Electrical Feedback," filed Jun. 2, 1011, now U.S. Pat. No. 9,161,803, the disclosure of which is incorporated by reference herein. Various other suitable ways in which a motor or other electrically powered device may be incorporated into any of the devices herein will be apparent to those of ordinary skill in the art in view of the teachings herein.

Furthermore, it should be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

V. Miscellaneous

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure.

Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) an end effector comprising:
      (i) a first jaw, and
      (ii) a second jaw, wherein the first and second jaws are operable to clamp tissue therebetween; and
   (c) a shaft assembly extending between the body and the end effector, wherein the shaft assembly comprises:
      (i) a proximal shaft portion defining a longitudinal axis, and
      (ii) an articulation section extending between the proximal shaft portion and the end effector, wherein the articulation section is operable to provide lateral deflection of the end effector relative to the longitudinal axis, wherein the articulation section comprises:
         (A) a proximal section end coupled to the proximal shaft portion,
         (B) a distal section end coupled to the end effector, and
         (C) a flexible feature extending between the proximal and distal section ends, wherein a dimension of the flexible feature decreases distally such that the flexible feature is configured to enable a distal end of the articulation section to deflect laterally in response to a lesser input force than a proximal end of the articulation section.

2. The apparatus of claim 1, wherein the flexible feature comprises a spine.

3. The apparatus of claim 2, wherein the spine extends continuously from the proximal section end to the distal section end.

4. The apparatus of claim 2, wherein the spine has a width in a direction transverse to the longitudinal axis, wherein the width decreases distally.

5. The apparatus of claim 1, wherein a proximal end of the flexible feature has a first width and a distal end of the flexible feature has a different second width.

6. The apparatus of claim 5, wherein the second width is lesser than the first width.

7. The apparatus of claim 6, wherein the first width tapers in a distal direction to the second width.

8. The apparatus of claim 1, wherein the articulation section further includes a plurality of ribs spaced apart axially along the flexible feature.

9. The apparatus of claim 1, wherein the articulation section further comprises an integrally formed first longitudinal portion that defines a first lateral side of the articulation section, and an integrally formed second longitudinal portion that defines a second lateral side of the articulation section, wherein the first and second longitudinal portions are configured to mate from opposing sides of the longitudinal axis and thereby cooperate to define the articulation section.

10. The apparatus of claim 9, wherein the first longitudinal portion includes a first coupling feature, wherein the second longitudinal portion includes a second coupling feature configured to couple with the first coupling feature.

11. The apparatus of claim 9, wherein the first longitudinal portion includes a first plurality of ribs, wherein the second longitudinal portion includes a second plurality of ribs.

12. The apparatus of claim 1, wherein the articulation section further includes a plurality of channels extending longitudinally therethrough.

13. The apparatus of claim 1, further comprising a cutting member operable to cut tissue clamped between the first and second jaws.

14. The apparatus of claim 13, further comprising a translating member, wherein the cutting member is coupled to the translating member, wherein the articulation section further comprises a first channel extending longitudinally between the proximal and distal section ends, wherein the first channel is configured to slidably receive the translating member.

15. The apparatus of claim 14, further comprising an elongate articulation drive member coupled to the end effector and configured to drive movement of the articulation section, wherein the articulation section further comprises a second channel extending longitudinally between the proximal and distal section ends, wherein the second channel is configured to slidably receive the elongate articulation drive member.

16. An apparatus comprising:
   (a) a body;
   (b) an end effector comprising:
      (i) a first jaw, and
      (ii) a second jaw, wherein the first and second jaws are operable to clamp tissue therebetween; and
   (c) a shaft assembly extending between the body and the end effector, wherein the shaft assembly comprises:
      (i) a proximal shaft portion defining a longitudinal axis, and
      (ii) an articulation section extending between the proximal shaft portion and the end effector, wherein the articulation section is operable to provide lateral deflection of the end effector relative to the longitudinal axis, wherein the articulation section comprises:

(A) a proximal section end coupled to the proximal shaft portion,
(B) a distal section end coupled to the end effector, and
(C) a flexible feature extending continuously from the proximal section end to the distal section end wherein the flexible feature has a first width at the proximal section end and a different second width at the distal section end.

17. The apparatus of claim 16, wherein the second width is lesser than the first width.

18. The apparatus of claim 17, wherein the flexible feature comprises a spine that tapers from the first width to the second width.

19. An apparatus comprising:
(a) a body;
(b) an end effector comprising:
   (i) a first jaw having a first electrode, and
   (ii) a second jaw having a second electrode, wherein the first and second jaws are operable to clamp tissue therebetween and apply bipolar RF energy to the clamped tissue with the first and second electrodes; and
(c) a shaft assembly extending between the body and the end effector, wherein the shaft assembly comprises:
   (i) a proximal shaft portion defining a longitudinal axis, and
   (ii) an articulation section extending between the proximal shaft portion and the end effector, wherein the articulation section is operable to provide lateral deflection of the end effector relative to the longitudinal axis, wherein the articulation section comprises:
      (A) a proximal section end coupled to the proximal shaft portion,
      (B) a distal section end coupled to the end effector, and
      (C) a flexible spine extending between the proximal and distal section ends, wherein the flexible spine has a dimension that decreases distally.

20. The apparatus of claim 19, wherein the flexible spine extends continuously from the proximal section end to the distal section end.

* * * * *